United States Patent
Saito et al.

(10) Patent No.: US 10,227,596 B2
(45) Date of Patent: Mar. 12, 2019

(54) TRANSLATIONAL CONTROL SYSTEM USING RNA-PROTEIN INTERACTION MOTIF

(71) Applicant: KYOTO UNIVERSITY, Kyoto (JP)

(72) Inventors: Hirohide Saito, Kyoto (JP); Kei Endo, Kyoto (JP); Tan Inoue, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/245,537

(22) Filed: Aug. 24, 2016

(65) Prior Publication Data

US 2017/0051292 A1 Feb. 23, 2017

Related U.S. Application Data

(62) Division of application No. 14/415,009, filed as application No. PCT/JP2013/069958 on Jul. 16, 2013, now Pat. No. 9,458,466.

(60) Provisional application No. 61/672,219, filed on Jul. 16, 2012.

(51) Int. Cl.
*C12N 15/67* (2006.01)
*C07H 21/04* (2006.01)

(52) U.S. Cl.
CPC .................. *C12N 15/67* (2013.01)

(58) Field of Classification Search
None
See application file for complete search history.

(56) References Cited

U.S. PATENT DOCUMENTS

| 2006/0134629 | A1* | 6/2006 | Link | C12N 15/1082 |
| | | | | 435/6.12 |
| 2011/0040077 | A1 | 2/2011 | Inoue et al. | |
| 2011/0245326 | A1 | 10/2011 | Belmont et al. | |

FOREIGN PATENT DOCUMENTS

WO    WO 2009/066757 A1    5/2009

OTHER PUBLICATIONS

Saito et al in Synthetic translational regulation by an L7Ae-kink-turn RNP switch and Supplementary Information (Nat. Chem. Biol. vol. 6, pp. 71-78 ; 2010; published online Dec. 13, 2009) (Year: 2009).*
Ho & Strauss III (BMC Biotechnology 2004, vol. 4, No. 10, pp. 1-5). (Year: 2004).*
Kang et al (J. Microbiol. Biotechnol. 2005 vol. 15, No. 3, pp. 544-550) (Year: 2005).*
Saito et al in Synthetic translational regulation by an L7Ae-kink-turn RNP switch and Supplementary Information (Nat. Chem. Biol. vol. 6, pp. 71-78: Supp Info pp. 1-44; 2010; published online Dec. 13, 2009) (Year: 2009).*
Goossen et al., "Translational repression by a complex between the iron-responsive element of ferritin mRNA and its specific cytoplasmic binding protein is position-dependent in vivo," The EMBO Journal, 1990, 9(12):4127-4133.
Babiskin et al., "Synthetic RNA modules for fine-tuning gene expression levels in yeast by modulating RNase III activity," Nucleic Acids Research, 2011, 39(19):8651-8664.
Bevan, Sian Claire, "Translational Regulation of Neuronal Nitric Oxide Synthase (nNOS)," Thesis, Department of Medical Biophysics, University of Toronto, 2007.
Cerny et al., "RNA-binding protein-mediated translational repression of transgene expression in plants," Plant Molecular Biology, 2003, 52:357-369.
Deans et al., "A Tunable Genetic Switch Based on RNAi and Repressor Proteins for Regulating Gene Expression in Mammalian Cells," Cell, 130, Jul. 27, 2007, 363-372.
Eberle et al., "Posttranscriptional Gene Regulation by Spatial Rearrangement of the 3' Untranslated Region," PLoS Biology, 2008, 6(4):e92:948-859.
Endo et al., "Quantitative and simultaneous translational control of distinct mammalian mRNAs," Nucleic Acids Research, 2013, 41(13):e135:1-12.
Goossen et al., "Position Is the Critical Determinant for Function of Iron-Responsive Elements as Translational Regulators," Molecular and Cellular Biology, May 1992, 12(5):1959-1966.
Moore et al., "Molecular Basis of Box C/D RNA-Protein Interactions: Cocrystal Structure of Archaeal L7Ae and a Box C/D RNA," Structure, May 2004, 12:807-818.
Saito et al., "Synthetic translational regulation by an L7Ae-kink-turn RNP switch," Nature Chemical Biology, Jan. 2010, 6:71-78.
Saito et al., "Synthetic human cell fate regulation by protein-driven RNA switches," Nat. Commun., 2011, 2(160):1-8.
SenGupta et al., "A three-hybrid system to detect RNA-protein interactions in vivo," Proc. Natl. Acad. Sci. USA, Aug. 1996, 93:8496-8501.
Wen et al., "Nonsense-mediated mRNA decay," Biochemical Society Transactions, 2008, 36(3):514-516.
Zhang et al., "Nonsense-mediated decay targets have multiple sequence-related features that can inhibit translation," Molecular Systems Biology, 2010, 6(442):1-9.
Office Action dated Jan. 30, 2018, in Japanese Application No. 2015-502983, with English machine translation.

* cited by examiner

*Primary Examiner* — Catherine S Hibbert
(74) *Attorney, Agent, or Firm* — Foley & Lardner LLP

(57) ABSTRACT

A translational control method using an RNA-protein interaction motif is provided. The method comprises a step of introducing an mRNA having: a 5'UTR regulation structure comprising: (1) a cap structure at the 5' terminus, (2) a spacer positioned on the 3' side of the cap structure, and (3) one or more RNA motifs positioned on the 3' side of the spacer, which comprises an RNA-protein interaction motif-derived nucleotide sequence or a variant thereof; and a nucleotide sequence encoding a target protein gene on the 3' side of the 5'UTR regulation structure, into a cell in the presence of a protein specifically binding to the RNA motifs, wherein a translational level is decreased as the number of bases of the spacer decreases, and the translational level is decreased as the number of the RNA motifs increases.

4 Claims, 15 Drawing Sheets

Specification includes a Sequence Listing.

K-loop (Kl)

Kl2

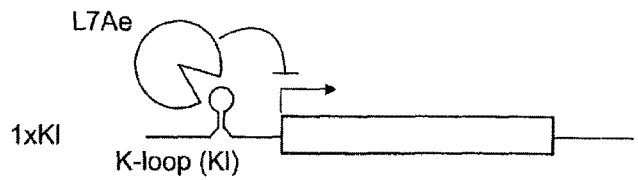
FIG.6(A)  1xKl
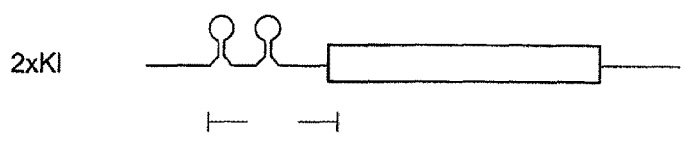
FIG.6(B)  2xKl
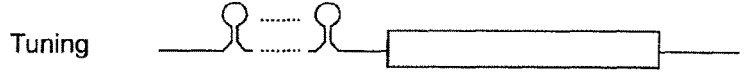
FIG.6(C)  Tuning
FIG.7
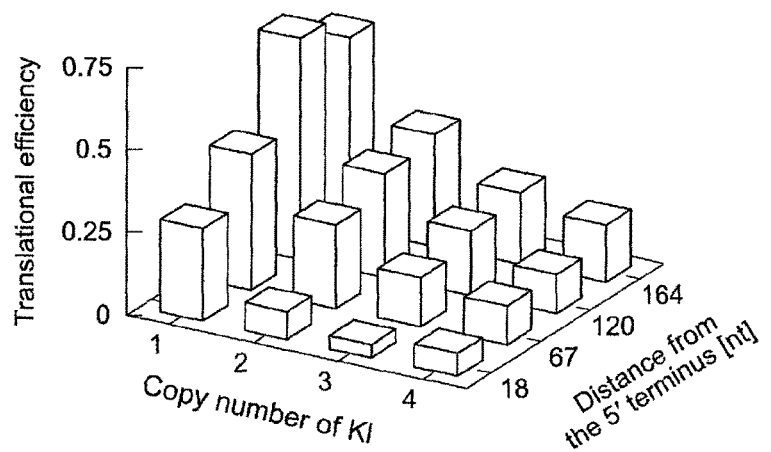

MS2 stem-loop (MS2SL)

BS15 biniding motif (Fr15)

FIG. 17(A)
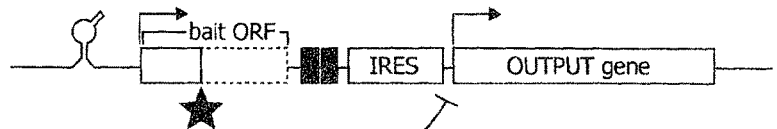
FIG. 17(B)
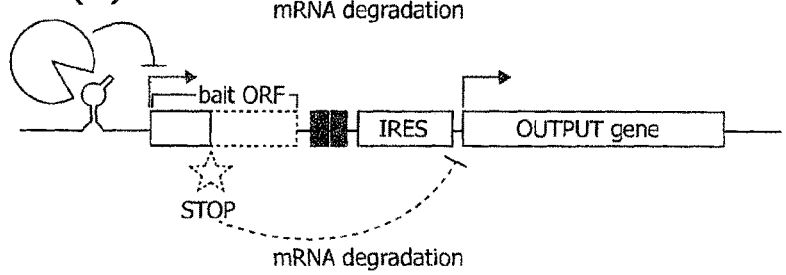
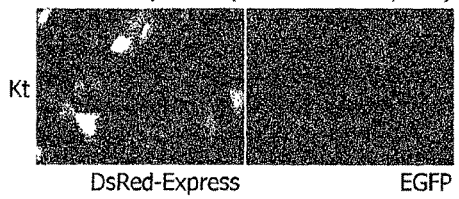
FIG. 18(A)
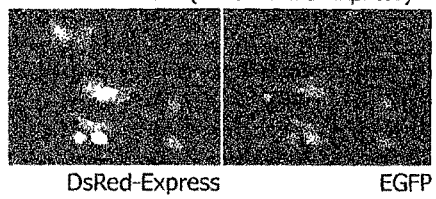
FIG. 18(C)
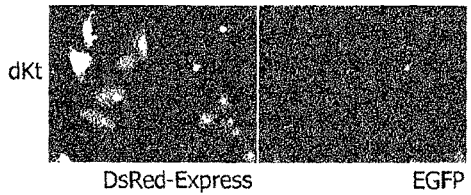
FIG. 18(B)
FIG. 18(D)
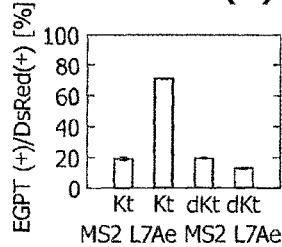
FIG. 18(E)
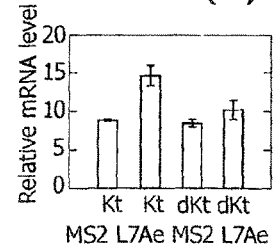
FIG. 18(F)

FIG.19(A)
FIG.19(B)
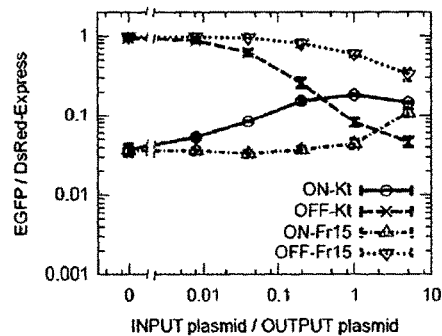
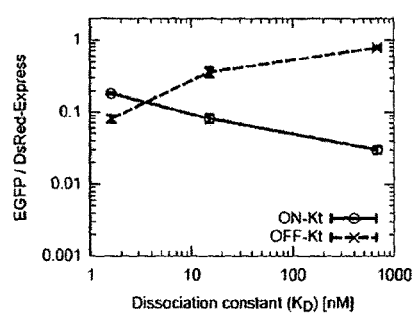
FIG.19(C)
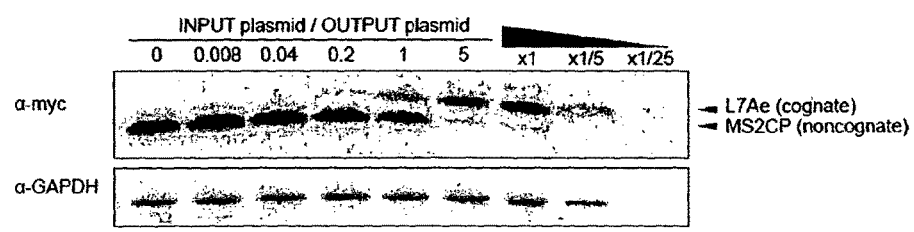
FIG.19(D)
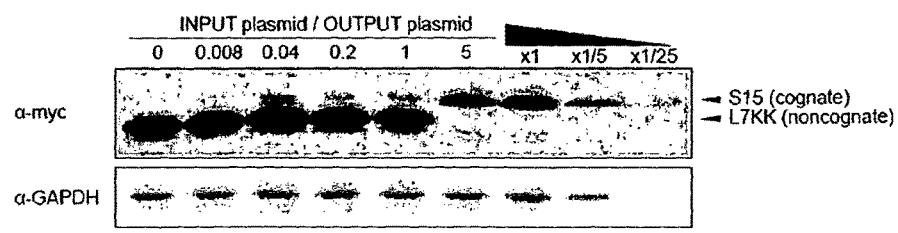

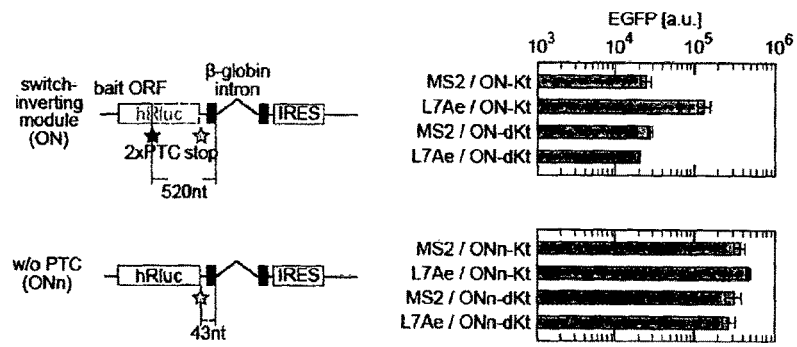
FIG. 20(B)
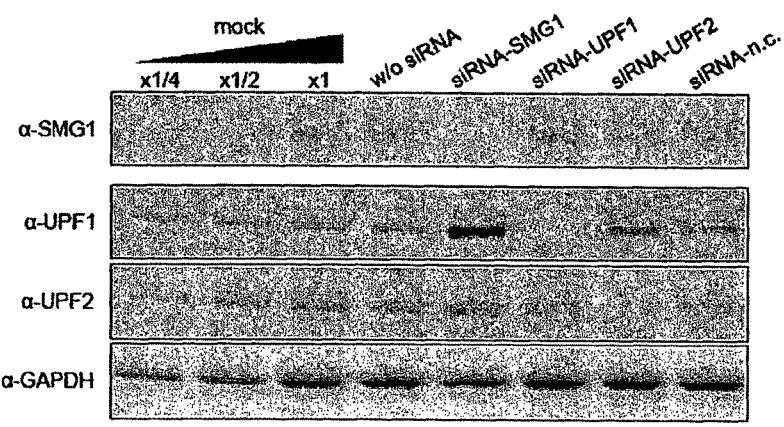
FIG. 20(C)
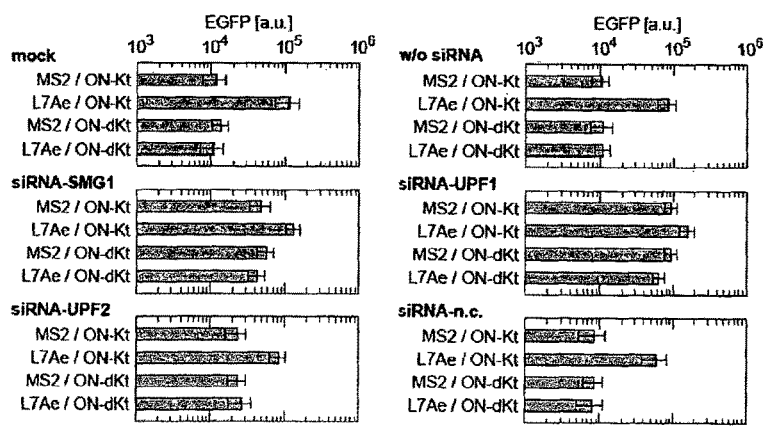

FIG.21(A)
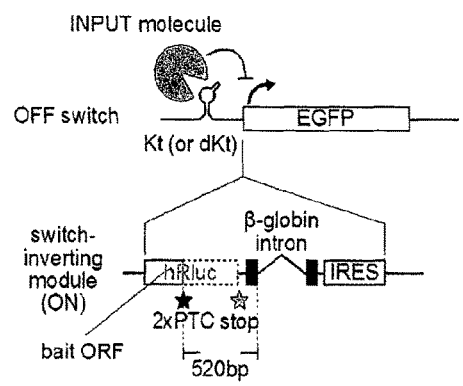
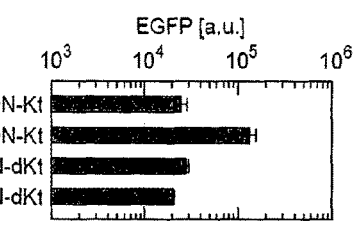
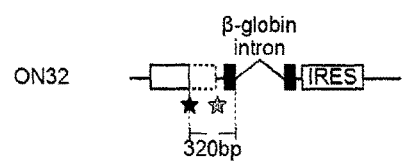
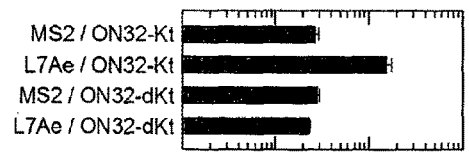
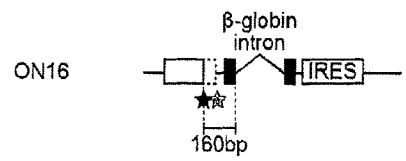
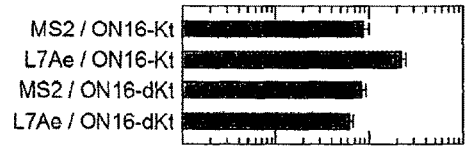
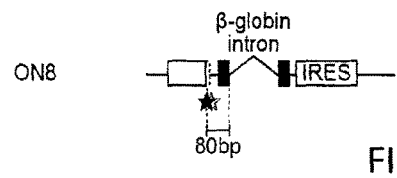
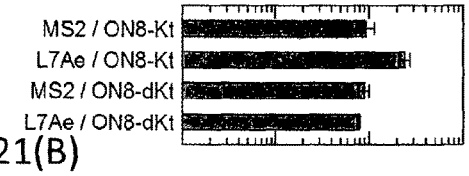
FIG.21(B)
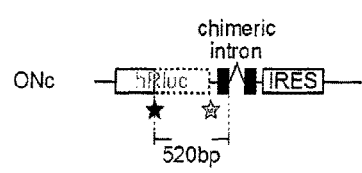
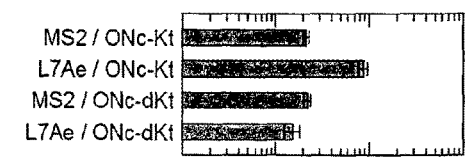

SEQUENCE LISTING

<160> NUMBER OF SEQ ID NOS: 84

<210> SEQ ID NO 1
<211> LENGTH: 23
<212> TYPE: RNA
<213> ORGANISM: Artificial Sequence
<220> FEATURE:
<223> OTHER INFORMATION: fragment

<400> SEQUENCE: 1
gggcgugaug cgaaagcuga ccc                                          23

<210> SEQ ID NO 2
<211> LENGTH: 34
<212> TYPE: RNA
<213> ORGANISM: Artificial Sequence
<220> FEATURE:
<223> OTHER INFORMATION: fragment -continued

```
<400> SEQUENCE: 2
agauccgggu gugaacggug aucacccgag aucc                                34

<210> SEQ ID NO 3
<211> LENGTH: 45
<212> TYPE: RNA
<213> ORGANISM: Artificial Sequence
<220> FEATURE:
<223> OTHER INFORMATION: fragment

<400> SEQUENCE: 3
agauccggac guacguguga acggugauca cguacgccga gaucc                    45

<210> SEQ ID NO 4
<211> LENGTH: 30
<212> TYPE: RNA
<213> ORGANISM: Artificial Sequence
<220> FEATURE:
<223> OTHER INFORMATION: fragment

<400> SEQUENCE: 4
agauccggug aggaucaccc aucgagaucc                                     30

<210> SEQ ID NO 5
<211> LENGTH: 70
<212> TYPE: RNA
<213> ORGANISM: Artificial Sequence
<220> FEATURE:
<223> OTHER INFORMATION: fragment

<400> SEQUENCE: 5
agauccucgg ucgaaagacu ugagggcagg ugagaggacu ucggucuggc accugcaccu    60
gacgagaucc                                                           70

<210> SEQ ID NO 6
<211> LENGTH: 37
<212> TYPE: RNA
<213> ORGANISM: Artificial Sequence
<220> FEATURE:
<223> OTHER INFORMATION: fragment

<400> SEQUENCE: 6
ggcguaugug aucuuucgug ugggucacca cugcgcc                             37

<210> SEQ ID NO 7
<211> LENGTH: 50
<212> TYPE: RNA
<213> ORGANISM: Artificial Sequence
<220> FEATURE:
<223> OTHER INFORMATION: fragment

<400> SEQUENCE: 7
gggugcuucg agcguaggaa gaaagccggg ggcugcagau aauguauagc               50

<210> SEQ ID NO 8
<211> LENGTH: 18
<212> TYPE: RNA
<213> ORGANISM: Artificial Sequence
<220> FEATURE:
<223> OTHER INFORMATION: fragment

<400> SEQUENCE: 8
ucagauccgc uaggaucu                                                  18
```

```
<210> SEQ ID NO 9
<211> LENGTH: 32
<212> TYPE: RNA
<213> ORGANISM: Artificial Sequence
<220> FEATURE:
<223> OTHER INFORMATION: fragment

<400> SEQUENCE: 9
ucagauccgc uagcgcuacc ggacucagau cu                                      32

<210> SEQ ID NO 10
<211> LENGTH: 51
<212> TYPE: RNA
<213> ORGANISM: Artificial Sequence
<220> FEATURE:
<223> OTHER INFORMATION: fragment

<400> SEQUENCE: 10
ucagauccgc uagccgccug uuuugaccgc ugggaucugc cauugagauc u                 51

<210> SEQ ID NO 11
<211> LENGTH: 67
<212> TYPE: RNA
<213> ORGANISM: Artificial Sequence
<220> FEATURE:
<223> OTHER INFORMATION: fragment

<400> SEQUENCE: 11
ucagauccgc uagcccgacc gccuuacugc cgccuguuuu gaccgcuggg aucugccauu        60
gagaucu                                                                  67

<210> SEQ ID NO 12
<211> LENGTH: 94
<212> TYPE: RNA
<213> ORGANISM: Artificial Sequence
<220> FEATURE:
<223> OTHER INFORMATION: fragment

<400> SEQUENCE: 12
ucagauccgc uagcucggau uagggccgca agaaaacuau cccgaccgcc uuacugccgc        60
cuguuuugac cgcugggauc ugccauugag aucu                                    94

<210> SEQ ID NO 13
<211> LENGTH: 120
<212> TYPE: RNA
<213> ORGANISM: Artificial Sequence
<220> FEATURE:
<223> OTHER INFORMATION: fragment

<400> SEQUENCE: 13
ucagauccgc uagcgcaggu agcagagcgg guaaacuggc ucggauuagg gccgcaagaa        60
aacuaucccg accgccuuac ugccgccugu uuugaccgcu gggaucugcc auugagaucu       120

<210> SEQ ID NO 14
<211> LENGTH: 145
<212> TYPE: RNA
<213> ORGANISM: Artificial Sequence
<220> FEATURE:
<223> OTHER INFORMATION: fragment

<400> SEQUENCE: 14
ucagauccgc uagcggauug gccugaacug ccagcuggcg cagguagcag agcggguaaa        60
cuggcucgga uuagggccgc aagaaaacua ucccgaccgc cuuacugccg ccuguuuuga       120
```

-continued

```
ccgcugggau cugccauuga gaucu                                            145

<210> SEQ ID NO 15
<211> LENGTH: 164
<212> TYPE: RNA
<213> ORGANISM: Artificial Sequence
<220> FEATURE:
<223> OTHER INFORMATION: fragment

<400> SEQUENCE: 15
ucagauccgc uagcgauaca ccgcauccgg cgcggauugg ccugaacugc cagcuggcgc       60
agguagcaga gcgdguaaac uggcucggau uagggccgca agaaaacuau cccgaccgcc      120
uuacugccgc cuguuuugac cgcugggauc ugccauugag aucu                       164

<210> SEQ ID NO 16
<211> LENGTH: 320
<212> TYPE: RNA
<213> ORGANISM: Artificial Sequence
<220> FEATURE:
<223> OTHER INFORMATION: fragment

<400> SEQUENCE: 16
ucagauccgc uagcgauaca ccgcauccgg cgcggauugg ccugaacugc cagcuggcgc       60
agguagcaga gcgdguaaac uggcucggau uagggccgca agaaaacuau cccgaccgcc      120
uuacugccgc cuguuuugac cgcugggauc ugccauugag auccgauccc gucguuuuac      180
aacgucguga cugggaaaac ccuggcguua cccaacuuaa ucgccuugca gcaucccc       240 cuuucgccag cuggcguaau agcgaagagg cccgcaccga ucgcccuucc aacaguugc       300 gcagccugac cgguagaucu                                                  320

<210> SEQ ID NO 17
<211> LENGTH: 936
<212> TYPE: DNA
<213> ORGANISM: Artificial Sequence
<220> FEATURE:
<223> OTHER INFORMATION: mutant ORF

<400> SEQUENCE: 17
atggcttcca aggtgtacga ccccgagcaa cgcaaacgca tgatcactgg gcctcagtgg       60
tgggctcgct gcaagcaaat gaacgtgctg gactccttca tcaactacta tgattccgag      120
aagcacgccg agaacgccgt gatttttctg catggtaacg ctgcctccag ctacctgtgg      180
aggcacgtcg tgcctcacat cgagcccgtg gctagatgca tcatccctga tctgatcgga      240
atgggtaagt ccggcaagag cgggaatggc tcatatcgcc tcctggatca ctacaagtac      300
ctcaccgctt ggttcgagct gctgaacctt ccaaagaaaa tcatctttgt gggccacgac      360
tggggggctt gtctggcctt tcactactcc tacgagcacc aagacaagat caaggccatc      420
gtccatgctg agagtgtcgt ggacgtgatc gagtcctgag acgagtgacc tgacatcgag      480
gaggatatcg ccctgatcaa gagcgaagag ggcgagaaaa tggtgcttga gataacttc      540 ttcgtcgaga ccatgctccc aagcaagatc atgcggaaac tggagcctga ggagttcgct      600
gcctacctgg agccattcaa ggagaagggc gaggttagac ggcctaccct tcctggcct      660 cgcgagatcc ctctcgttaa gggaggcaag cccgacgtcg tccagattgt ccgcaactac      720
aacgcctacc ttcgggccag cgacgatctg cctaagatgt tcatcgagtc cgaccctggg      780
ttcttttcca acgctattgt cgagggagct aagaagttcc ctaacaccga gttcgtgaag      840
```

```
gtgaagggcc tccacttcag ccaggaggac gctccagatg aaatgggtaa gtacatcaag    900
agcttcgtgg agcgcgtgct gaagaacgag cagtaa                              936
```

<210> SEQ ID NO 18
<211> LENGTH: 552
<212> TYPE: DNA
<213> ORGANISM: Homo sapiens

<400> SEQUENCE: 18

```
atcgatcctg agaacttcag ggtgagtcta tgggacccct tgatgttttct ttccccttct    60 tttctatggt taagttcatg tcataggaag gggagaagta acagggtaca catattgacc    120 aaatcaggt aattttgcat ttgtaatttt aaaaaatgct ttcttctttt aatatacttt     180
tttgtttatc ttatttctaa tactttccct aatctctttc tttcagggca ataatgatac    240
aatgtatcat gcctctttgc accattctaa agaataacag tgataatttc tgggttaagg    300
caatagcaat atttctgcat ataaatattt ctgcatataa attgtaactg atgtaagagg    360
tttcatattg ctaatagcag ctacaatcca gctaccattc tgcttttatt ttatggttgg    420
gataaggctg gattattctg agtccaagct aggcccttt gctaatcatg ttcatacctc     480
ttatcttcct cccacagctc ctgggcaacg tgctggtctg tgtgctggcc catcactttg    540
gcaaagcacg tg                                                        552
```

<210> SEQ ID NO 19
<211> LENGTH: 78
<212> TYPE: RNA
<213> ORGANISM: Artificial Sequence
<220> FEATURE:
<223> OTHER INFORMATION: fragment

<400> SEQUENCE: 19

```
ucagauccgc uagcgcuacc ggacucagau cuggggcgug auccgaaagg ugacccggau    60
ccaccggucg ccaccaug                                                   78
```

<210> SEQ ID NO 20
<211> LENGTH: 210
<212> TYPE: RNA
<213> ORGANISM: Artificial Sequence
<220> FEATURE:
<223> OTHER INFORMATION: fragment

<400> SEQUENCE: 20

```
ucagauccgc uagcgauaca ccgcauccgg cgcggauugg ccugaacugc cagcuggcgc    60
agguagcaga gcggguaaac uggcucggau uagggccgca agaaaacuau cccgaccgcc    120
uuacugccgc cuguuuugac cgcugggauc ugccauugag aucggggcg ugauccgaaa     180 ggugacccgg auccaccggu cgccaccaug                                     210
```

<210> SEQ ID NO 21
<211> LENGTH: 222
<212> TYPE: RNA
<213> ORGANISM: Artificial Sequence
<220> FEATURE:
<223> OTHER INFORMATION: fragment

<400> SEQUENCE: 21

```
ucagauccgc uagcgcuacc ggacucagau cuggggcgug auccgaaagg ugacccggau    60
ccgaucccgu cguuuuacaa cgucgugacu gggaaaaccc uggcguuacc caacuuaauc    120
gccuugcagc acauccccu uucgccagcu ggcguaauag cgaagaggcc cgcaccgauc    180
```

```
gcccuuccca acaguugcgc agccugaccg gucgccacca ug            222
```

<210> SEQ ID NO 22
<211> LENGTH: 64
<212> TYPE: RNA
<213> ORGANISM: Artificial Sequence
<220> FEATURE:
<223> OTHER INFORMATION: fragment

<400> SEQUENCE: 22

```
ucagauccgc uaggaucugg ggcgugaucc gaaaggugac ccggauccac cggucgccac   60
caug                                                                64
```

<210> SEQ ID NO 23
<211> LENGTH: 97
<212> TYPE: RNA
<213> ORGANISM: Artificial Sequence
<220> FEATURE:
<223> OTHER INFORMATION: fragment

<400> SEQUENCE: 23

```
ucagauccgc uagccgccug uuuugaccgc ugggaucugc cauugagauc uggggcguga   60
uccgaaaggu gacccggauc caccggucgc caccaug                           97
```

<210> SEQ ID NO 24
<211> LENGTH: 113
<212> TYPE: RNA
<213> ORGANISM: Artificial Sequence
<220> FEATURE:
<223> OTHER INFORMATION: fragment

<400> SEQUENCE: 24

```
ucagauccgc uagcccgacc gccuuacugc cgccuguuuu gaccgcuggg aucugccauu   60
gagaucuggg gcgugauccg aaaggugacc cggauccacc ggucgccacc aug         113
```

<210> SEQ ID NO 25
<211> LENGTH: 140
<212> TYPE: RNA
<213> ORGANISM: Artificial Sequence
<220> FEATURE:
<223> OTHER INFORMATION: fragment

<400> SEQUENCE: 25

```
ucagauccgc uagcucggau uagggccgca agaaaacuau cccgaccgcc uuacugccgc   60
cuguuuugac cgcugggauc ugccauugag aucggggcg ugauccgaaa ggugacccgg   120
auccaccggu cgccaccaug                                              140
```

<210> SEQ ID NO 26
<211> LENGTH: 166
<212> TYPE: RNA
<213> ORGANISM: Artificial Sequence
<220> FEATURE:
<223> OTHER INFORMATION: fragment

<400> SEQUENCE: 26

```
ucagauccgc uagcgcaggu agcagagcgg guaaacuggc ucggauuagg gccgcaagaa   60
aacuaucccg accgccuuac ugccgccugu uuugaccgcu gggaucugcc auugagaucu   120
ggggcgugau ccgaaaggug acccggaucc accggucgcc accaug                166
```

<210> SEQ ID NO 27

```
<211> LENGTH: 191
<212> TYPE: RNA
<213> ORGANISM: Artificial Sequence
<220> FEATURE:
<223> OTHER INFORMATION: fragment

<400> SEQUENCE: 27
ucagauccgc uagcggauug gccugaacug ccagcuggcg cagguagcag agcggguaaa    60
cuggcucgga uuagggccgc aagaaaacua ucccgaccgc cuuacugccg ccuguuuuga   120
ccgcugggau cugccauuga gaucuggggc gugauccgaa aggugacccg gauccaccgg   180
ucgccaccau g                                                        191

<210> SEQ ID NO 28
<211> LENGTH: 366
<212> TYPE: RNA
<213> ORGANISM: Artificial Sequence
<220> FEATURE:
<223> OTHER INFORMATION: fragment

<400> SEQUENCE: 28
ucagauccgc uagcgauaca ccgcauccgg cgcggauugg ccugaacugc cagcuggcgc    60
agguagcaga gcggguaaac uggcucggau uagggccgca agaaaacuau cccgaccgcc   120
uuacugccgc cuguuuugac cgcugggauc ugccauugag auccgauccc gucguuuuac   180
aacgucguga cuggaaaaac ccuggcguua cccaacuuaa ucgccuugca gcaucccc     240 cuuucgccag cuggcguaau agcgaagagg cccgcaccga ucgcccuucc aacaguugc    300 gcagccugac cgguagaucu ggggcgugau ccgaaaggug acccggaucc accgucgcc    360 accaug                                                              366

<210> SEQ ID NO 29
<211> LENGTH: 62
<212> TYPE: RNA
<213> ORGANISM: Artificial Sequence
<220> FEATURE:
<223> OTHER INFORMATION: fragment

<400> SEQUENCE: 29
ucagauccgc uaggauccgg gugugaacgg ugaucacccg agauccaccg gucgccacca    60
ug                                                                   62

<210> SEQ ID NO 30
<211> LENGTH: 90
<212> TYPE: RNA
<213> ORGANISM: Artificial Sequence
<220> FEATURE:
<223> OTHER INFORMATION: fragment

<400> SEQUENCE: 30
ucagauccgc uaggauccgg gugugaacgg ugaucacccg agauccgggu gugaacggug    60
aucacccgag auccaccggu cgccaccaug                                     90

<210> SEQ ID NO 31
<211> LENGTH: 118
<212> TYPE: RNA
<213> ORGANISM: Artificial Sequence
<220> FEATURE:
<223> OTHER INFORMATION: fragment

<400> SEQUENCE: 31
ucagauccgc uaggauccgg gugugaacgg ugaucacccg agauccgggu gugaacggug    60
```

```
aucacccgag auccgggugu gaacggugau cacccgagau ccaccggucg ccaccaug        118
```

<210> SEQ ID NO 32
<211> LENGTH: 146
<212> TYPE: RNA
<213> ORGANISM: Artificial Sequence
<220> FEATURE:
<223> OTHER INFORMATION: fragment

<400> SEQUENCE: 32

```
ucagauccgc uaggauccgg gugugaacgg ugaucacccg agauccgggu gugaacggug        60
aucacccgag auccgggugu gaacggugau cacccgagau ccggguguga acggugauca       120
cccgagaucc accggucgcc accaug                                            146
```

<210> SEQ ID NO 33
<211> LENGTH: 111
<212> TYPE: RNA
<213> ORGANISM: Artificial Sequence
<220> FEATURE:
<223> OTHER INFORMATION: fragment

<400> SEQUENCE: 33

```
ucagauccgc uagcccgacc gccuuacugc cgccuguuuu gaccgcuggg aucugccauu        60
gagauccggg ugugaacggu gaucacccga gauccaccgg ucgccaccau g               111
```

<210> SEQ ID NO 34
<211> LENGTH: 139
<212> TYPE: RNA
<213> ORGANISM: Artificial Sequence
<220> FEATURE:
<223> OTHER INFORMATION: fragment

<400> SEQUENCE: 34

```
ucagauccgc uagcccgacc gccuuacugc cgccuguuuu gaccgcuggg aucugccauu        60
gagauccggg ugugaacggu gaucacccga gauccgggug ugaacgguga ucacccgaga       120
uccaccgguc gccaccaug                                                    139
```

<210> SEQ ID NO 35
<211> LENGTH: 167
<212> TYPE: RNA
<213> ORGANISM: Artificial Sequence
<220> FEATURE:
<223> OTHER INFORMATION: fragment

<400> SEQUENCE: 35

```
ucagauccgc uagcccgacc gccuuacugc cgccuguuuu gaccgcuggg aucugccauu        60
gagauccggg ugugaacggu gaucacccga gauccgggug ugaacgguga ucacccgaga       120 uccggguguga aacggugauc acccgagauc caccggucgc caccaug                    167
```

<210> SEQ ID NO 36
<211> LENGTH: 195
<212> TYPE: RNA
<213> ORGANISM: Artificial Sequence
<220> FEATURE:
<223> OTHER INFORMATION: fragment

<400> SEQUENCE: 36

```
ucagauccgc uagcccgacc gccuuacugc cgccuguuuu gaccgcuggg aucugccauu        60
gagauccggg ugugaacggu gaucacccga gauccgggug ugaacgguga ucacccgaga       120
```

```
uccgggugug aacggugauc acccgagauc cgggugugaa cggugaucac ccgagaucca      180
ccggucgcca ccaug                                                       195
```

<210> SEQ ID NO 37
<211> LENGTH: 164
<212> TYPE: RNA
<213> ORGANISM: Artificial Sequence
<220> FEATURE:
<223> OTHER INFORMATION: fragment

<400> SEQUENCE: 37

```
ucagauccgc uagcgcaggu agcagagcgg guaaacuggc ucggauuagg gccgcaagaa       60
aacuaucccg accgccuuac ugccgccugu uuugaccgcu gggaucugcc auugagaucc      120
gggugugaac ggugaucacc cgagauccac cggucgccac caug                       164
```

<210> SEQ ID NO 38
<211> LENGTH: 192
<212> TYPE: RNA
<213> ORGANISM: Artificial Sequence
<220> FEATURE:
<223> OTHER INFORMATION: fragment

<400> SEQUENCE: 38

```
ucagauccgc uagcgcaggu agcagagcgg guaaacuggc ucggauuagg gccgcaagaa       60
aacuaucccg accgccuuac ugccgccugu uuugaccgcu gggaucugcc auugagaucc      120
gggugugaac ggugaucacc cgagauccgg gugugaacgg ugaucacccg agauccaccg      180
gucgccacca ug                                                          192
```

<210> SEQ ID NO 39
<211> LENGTH: 220
<212> TYPE: RNA
<213> ORGANISM: Artificial Sequence
<220> FEATURE:
<223> OTHER INFORMATION: fragment

<400> SEQUENCE: 39

```
ucagauccgc uagcgcaggu agcagagcgg guaaacuggc ucggauuagg gccgcaagaa       60
aacuaucccg accgccuuac ugccgccugu uuugaccgcu gggaucugcc auugagaucc      120
gggugugaac ggugaucacc cgagauccgg gugugaacgg ugaucacccg agauccgggu      180
gugaacggug aucacccgag auccaccggu cgccaccaug                            220
```

<210> SEQ ID NO 40
<211> LENGTH: 248
<212> TYPE: RNA
<213> ORGANISM: Artificial Sequence
<220> FEATURE:
<223> OTHER INFORMATION: fragment

<400> SEQUENCE: 40

```
ucagauccgc uagcgcaggu agcagagcgg guaaacuggc ucggauuagg gccgcaagaa       60
aacuaucccg accgccuuac ugccgccugu uuugaccgcu gggaucugcc auugagaucc      120
gggugugaac ggugaucacc cgagauccgg gugugaacgg ugaucacccg agauccgggu      180
gugaacggug aucacccgag auccgggugu gaacggugau cacccgagau ccaccggucg      240
ccaccaug                                                               248
```

<210> SEQ ID NO 41
<211> LENGTH: 208

-continued

```
<212> TYPE: RNA
<213> ORGANISM: Artificial Sequence
<220> FEATURE:
<223> OTHER INFORMATION: fragment

<400> SEQUENCE: 41
ucagauccgc uagcgauaca ccgcauccgg cgcggauugg ccugaacugc cagcuggcgc      60
agguagcaga gcgdgguaaac uggcucggau uagggccgca agaaaacuau cccgaccgcc    120
uuacugccgc cuguuuugac cgcugggauc ugccauugag auccgggugu gaacggugau    180
cacccgagau ccaccggucg ccaccaug                                        208

<210> SEQ ID NO 42
<211> LENGTH: 236
<212> TYPE: RNA
<213> ORGANISM: Artificial Sequence
<220> FEATURE:
<223> OTHER INFORMATION: fragment

<400> SEQUENCE: 42
ucagauccgc uagcgauaca ccgcauccgg cgcggauugg ccugaacugc cagcuggcgc      60
agguagcaga gcgdgguaaac uggcucggau uagggccgca agaaaacuau cccgaccgcc    120
uuacugccgc cuguuuugac cgcugggauc ugccauugag auccgggugu gaacggugau    180
cacccgagau ccgggguguga acggugauca cccgagaucc accggucgcc accaug        236

<210> SEQ ID NO 43
<211> LENGTH: 264
<212> TYPE: RNA
<213> ORGANISM: Artificial Sequence
<220> FEATURE:
<223> OTHER INFORMATION: fragment

<400> SEQUENCE: 43
ucagauccgc uagcgauaca ccgcauccgg cgcggauugg ccugaacugc cagcuggcgc      60
agguagcaga gcgdgguaaac uggcucggau uagggccgca agaaaacuau cccgaccgcc    120
uuacugccgc cuguuuugac cgcugggauc ugccauugag auccgggugu gaacggugau    180
cacccgagau ccgggguguga acggugauca cccgagaucc gggugugaac ggugaucacc    240
cgagauccac cggucgccac caug                                            264

<210> SEQ ID NO 44
<211> LENGTH: 292
<212> TYPE: RNA
<213> ORGANISM: Artificial Sequence
<220> FEATURE:
<223> OTHER INFORMATION: fragment

<400> SEQUENCE: 44
ucagauccgc uagcgauaca ccgcauccgg cgcggauugg ccugaacugc cagcuggcgc      60
agguagcaga gcgdgguaaac uggcucggau uagggccgca agaaaacuau cccgaccgcc    120
uuacugccgc cuguuuugac cgcugggauc ugccauugag auccgggugu gaacggugau    180
cacccgagau ccgggguguga acggugauca cccgagaucc gggugugaac ggugaucacc    240
cgagauccgg gugugaacgg ugaucacccg agauccaccg gucgccacca ug             292

<210> SEQ ID NO 45
<211> LENGTH: 87
<212> TYPE: RNA
<213> ORGANISM: Artificial Sequence
<220> FEATURE:
```

<223> OTHER INFORMATION: fragment

<400> SEQUENCE: 45
ucagauccgc uagcgcuacc ggacucagau ccggacguac gugugaacgg ugaucacgua    60
cgccgagauc caccggucgc caccaug    87

<210> SEQ ID NO 46
<211> LENGTH: 126
<212> TYPE: RNA
<213> ORGANISM: Artificial Sequence
<220> FEATURE:
<223> OTHER INFORMATION: fragment

<400> SEQUENCE: 46
ucagauccgc uagcgcuacc ggacucagau ccggacguac gugugaacgg ugaucacgua    60
cgccgagauc cggacguacg ugugaacggu gaucacguac gccgagaucc accggucgcc    120
accaug    126

<210> SEQ ID NO 47
<211> LENGTH: 58
<212> TYPE: RNA
<213> ORGANISM: Artificial Sequence
<220> FEATURE:
<223> OTHER INFORMATION: fragment

<400> SEQUENCE: 47
ucagauccgc uaggauccgg ugaggaucac ccaucgagau ccaccggucg ccaccaug    58

<210> SEQ ID NO 48
<211> LENGTH: 82
<212> TYPE: RNA
<213> ORGANISM: Artificial Sequence
<220> FEATURE:
<223> OTHER INFORMATION: fragment

<400> SEQUENCE: 48
ucagauccgc uaggauccgg ugaggaucac ccaucgagau ccggugagga ucacccaucg    60
agauccaccg gucgccacca ug    82

<210> SEQ ID NO 49
<211> LENGTH: 107
<212> TYPE: RNA
<213> ORGANISM: Artificial Sequence
<220> FEATURE:
<223> OTHER INFORMATION: fragment

<400> SEQUENCE: 49
ucagauccgc uagcccgacc gccuuacugc cgccuguuuu gaccgcuggg aucugccauu    60
gagauccggu gaggaucacc caucgagauc caccggucgc caccaug    107

<210> SEQ ID NO 50
<211> LENGTH: 131
<212> TYPE: RNA
<213> ORGANISM: Artificial Sequence
<220> FEATURE:
<223> OTHER INFORMATION: fragment

<400> SEQUENCE: 50
ucagauccgc uagcccgacc gccuuacugc cgccuguuuu gaccgcuggg aucugccauu    60
gagauccggu gaggaucacc caucgagauc cggugaggau cacccaucga gauccaccgg    120
ucgccaccau g    131

<210> SEQ ID NO 51
<211> LENGTH: 94
<212> TYPE: RNA
<213> ORGANISM: Artificial Sequence
<220> FEATURE:
<223> OTHER INFORMATION: fragment

<400> SEQUENCE: 51
ucagauccgc uaggauccuc ggucgaaaga cuugagggca ggagaggacu ucggucuggc    60
cugcaccuga cgagauccac cggucgccac caug                                94

<210> SEQ ID NO 52
<211> LENGTH: 154
<212> TYPE: RNA
<213> ORGANISM: Artificial Sequence
<220> FEATURE:
<223> OTHER INFORMATION: fragment

<400> SEQUENCE: 52
ucagauccgc uaggauccuc ggucgaaaga cuugagggca ggagaggacu ucggucuggc    60
cugcaccuga cgagauccuc ggucgaaaga cuugagggca ggagaggacu ucggucuggc   120
cugcaccuga cgagauccac cggucgccac caug                               154

<210> SEQ ID NO 53
<211> LENGTH: 143
<212> TYPE: RNA
<213> ORGANISM: Artificial Sequence
<220> FEATURE:
<223> OTHER INFORMATION: fragment

<400> SEQUENCE: 53
ucagauccgc uagcccgacc gccuuacugc cgccuguuuu gaccgcuggg aucugccauu    60
gagauccucg gucgaaagac uugagggcag gagaggacuu cggucuggcc ugcaccugac   120
gagauccacc ggucgccacc aug                                           143

<210> SEQ ID NO 54
<211> LENGTH: 203
<212> TYPE: RNA
<213> ORGANISM: Artificial Sequence
<220> FEATURE:
<223> OTHER INFORMATION: fragment

<400> SEQUENCE: 54
ucagauccgc uagcccgacc gccuuacugc cgccuguuuu gaccgcuggg aucugccauu    60
gagauccucg gucgaaagac uugagggcag gagaggacuu cggucuggcc ugcaccugac   120
gagauccucg gucgaaagac uugagggcag gagaggacuu cggucuggcc ugcaccugac   180
gagauccacc ggucgccacc aug                                           203

<210> SEQ ID NO 55
<211> LENGTH: 2104
<212> TYPE: DNA
<213> ORGANISM: Artificial Sequence
<220> FEATURE:
<223> OTHER INFORMATION: fragment

<400> SEQUENCE: 55
atggcttcca aggtgtacga ccccgagcaa cgcaaacgca tgatcactgg gcctcagtgg    60
tgggctcgct gcaagcaaat gaacgtgctg gactccttca tcaactacta tgattccgag   120

```
aagcacgccg agaacgccgt gattttctg catggtaacg ctgcctccag ctacctgtgg      180
aggcacgtcg tgcctcacat cgagcccgtg gctagatgca tcatccctga tctgatcgga      240
atgggtaagt ccggcaagag cgggaatggc tcatatcgcc tcctggatca ctacaagtac      300
ctcaccgctt ggttcgagct gctgaacctt ccaaagaaaa tcatctttgt gggccacgac      360
tggggggctt gtctggcctt tcactactcc tacgagcacc aagacaagat caaggccatc      420
gtccatgctg agagtgtcgt ggacgtgatc gagtcctgag acgagtgacc tgacatcgag      480
gaggatatcg ccctgatcaa gagcgaagag ggcgagaaaa tggtgcttga ataacttc       540
ttcgtcgaga ccatgctccc aagcaagatc atgcggaaac tggagcctga ggagttcgct      600
gcctacctgg agccattcaa ggagaagggc gaggttagac ggcctaccct tcctggcct      660
cgcgagatcc ctctcgttaa gggaggcaag cccgacgtcg tccagattgt ccgcaactac      720
aacgcctacc ttcgggccag cgacgatctg cctaagatgt tcatcgagtc cgaccctggg      780
ttcttttcca cgctattgt cgagggagct aagaagttcc ctaacaccga gttcgtgaag       840
gtgaagggcc tccacttcag ccaggaggac gctccagatg aaatgggtaa gtacatcaag      900
agcttcgtgg agcgcgtgct gaagaacgag cagtaattct agagtcgggg cggccgggat      960
cgatcctgag aacttcaggg tgagtctatg ggacccttga tgtttttcttt cccttcttt     1020
tctatggtta agttcatgtc ataggaaggg gagaagtaac agggtacaca tattgaccaa     1080
atcagggtaa ttttgcattt gtaattttaa aaaatgcttt cttcttttaa tatacttttt     1140
tgtttatctt atttctaata ctttccctaa tctctttctt tcagggcaat aatgatacaa     1200
tgtatcatgc ctcttgcac cattctaaag aataacagtg ataatttctg ggttaaggca     1260
atagcaatat ttctgcatat aaatatttct gcatataaat tgtaactgat gtaagaggtt     1320
tcatattgct aatagcagct acaatccagc taccattctg cttttattt atggttggga     1380
taaggctgga ttattctgag tccaagctag gccccttttgc taatcatgtt catacctctt     1440
atcttcctcc cacagctcct gggcaacgtg ctggtctgtg tgctggccca tcactttggc     1500
aaagcacgtg agatccgccc ctctcccctcc ccccccccta acgttactgg ccgaagccgc     1560
ttggaataag gccggtgtgc gtttgtctat atgttatttt ccaccatatt gccgtctttt     1620
ggcaatgtga gggcccggaa acctggccct gtcttcttga cgagcattcc tagggtctt     1680
tcccctctcg ccaaaggaat gcaaggtctg ttgaatgtcg tgaaggaagc agttcctctg     1740
gaagcttctt gaagacaaac aacgtctgta gcgacccttt gcaggcagcg gaaccccca     1800
cctggcgaca ggtgcctctg cggccaaaag ccacgtgtat aagatacacc tgcaaaggcg     1860
gcacaacccc agtgccacgt tgtgagttgg atagttgtgg aaagagtcaa atggctctcc     1920
tcaagcgtat tcaacaaggg gctgaaggat gcccagaagg taccccattg tatgggatct     1980
gatctggggc ctcggtgcac atgctttaca tgtgtttagt cgaggttaaa aaaacgtcta     2040
ggccccccga accacgggga cgtggttttc ctttgaaaaa cacgatgata atatggccac     2100
aacc                                                                  2104
```

<210> SEQ ID NO 56
<211> LENGTH: 29
<212> TYPE: DNA
<213> ORGANISM: Artificial Sequence
<220> FEATURE:
<223> OTHER INFORMATION: PCR primer

<400> SEQUENCE: 56

```
cccgggatcc gatcccgtcg ttttacaac                                         29
```

<210> SEQ ID NO 57
<211> LENGTH: 25
<212> TYPE: DNA
<213> ORGANISM: Artificial Sequence
<220> FEATURE:
<223> OTHER INFORMATION: PCR primer

<400> SEQUENCE: 57
agatctaccg gtcaggctgc gcaac                                          25

<210> SEQ ID NO 58
<211> LENGTH: 25
<212> TYPE: DNA
<213> ORGANISM: Artificial Sequence
<220> FEATURE:
<223> OTHER INFORMATION: PCR primner

<400> SEQUENCE: 58
ggatccgcta gcgatacacc gcatc                                          25

<210> SEQ ID NO 59
<211> LENGTH: 28
<212> TYPE: DNA
<213> ORGANISM: Artificial Sequence
<220> FEATURE:
<223> OTHER INFORMATION: PCR primer

<400> SEQUENCE: 59
actagtagat ctcaatggca gatcccag                                       28

<210> SEQ ID NO 60
<211> LENGTH: 33
<212> TYPE: DNA
<213> ORGANISM: Artificial Sequence
<220> FEATURE:
<223> OTHER INFORMATION: PCR primer

<400> SEQUENCE: 60
catgggatcc gggtgtgaac ggtgatcacc cga                                 33

<210> SEQ ID NO 61
<211> LENGTH: 33
<212> TYPE: DNA
<213> ORGANISM: Artificial Sequence
<220> FEATURE:
<223> OTHER INFORMATION: PCR primer

<400> SEQUENCE: 61
gatctcgggt gatcaccgtt cacacccgga tcc                                 33

<210> SEQ ID NO 62
<211> LENGTH: 44
<212> TYPE: DNA
<213> ORGANISM: Artificial Sequence
<220> FEATURE:
<223> OTHER INFORMATION: PCR primer

<400> SEQUENCE: 62
catgggatcc ggacgtacgt gtgaacggtg atcacgtacg ccga                     44

<210> SEQ ID NO 63
<211> LENGTH: 44
<212> TYPE: DNA
<213> ORGANISM: Artificial Sequence
<220> FEATURE:

```
<223> OTHER INFORMATION: PCR primer

<400> SEQUENCE: 63
gatctcggcg tacgtgatca ccgttcacac gtacgtccgg atcc                    44

<210> SEQ ID NO 64
<211> LENGTH: 29
<212> TYPE: DNA
<213> ORGANISM: Artificial Sequence
<220> FEATURE:
<223> OTHER INFORMATION: PCR primer

<400> SEQUENCE: 64
catgggatcc ggtgaggatc acccatcga                                     29

<210> SEQ ID NO 65
<211> LENGTH: 29
<212> TYPE: DNA
<213> ORGANISM: Artificial Sequence
<220> FEATURE:
<223> OTHER INFORMATION: PCR primer

<400> SEQUENCE: 65
gatctcgttg ggtgttcctc tccggatcc                                     29

<210> SEQ ID NO 66
<211> LENGTH: 80
<212> TYPE: DNA
<213> ORGANISM: Artificial Sequence
<220> FEATURE:
<223> OTHER INFORMATION: PCR template

<400> SEQUENCE: 66
gggatgtcag gtgcaggcca gaccgaagtc ctctcctgcc ctcaagtctt tcgaccatcc   60
ctatagtgag tcgtattagc                                               80

<210> SEQ ID NO 67
<211> LENGTH: 38
<212> TYPE: DNA
<213> ORGANISM: Artificial Sequence
<220> FEATURE:
<223> OTHER INFORMATION: PCR primer

<400> SEQUENCE: 67
gctaatccat gggatcctcg gtcgaaagac ttgagggc                           38

<210> SEQ ID NO 68
<211> LENGTH: 28
<212> TYPE: DNA
<213> ORGANISM: Artificial Sequence
<220> FEATURE:
<223> OTHER INFORMATION: PCR primer

<400> SEQUENCE: 68
cccagatctc gtcaggtgca ggccagac                                      28

<210> SEQ ID NO 69
<211> LENGTH: 23
<212> TYPE: DNA
<213> ORGANISM: Artificial Sequence
<220> FEATURE:
<223> OTHER INFORMATION: PCR primer

<400> SEQUENCE: 69
gtgacctgac atcgaggagg ata                                           23
```

```
<210> SEQ ID NO 70
<211> LENGTH: 22
<212> TYPE: DNA
<213> ORGANISM: Artificial Sequence
<220> FEATURE:
<223> OTHER INFORMATION: PCR primer

<400> SEQUENCE: 70
cgtctcagga ctcgatcacg tc                                              22

<210> SEQ ID NO 71
<211> LENGTH: 37
<212> TYPE: DNA
<213> ORGANISM: Artificial Sequence
<220> FEATURE:
<223> OTHER INFORMATION: PCR primer

<400> SEQUENCE: 71
gaatccatgg gatccatgta cgtgagattt gaggttc                              37

<210> SEQ ID NO 72
<211> LENGTH: 34
<212> TYPE: DNA
<213> ORGANISM: Artificial Sequence
<220> FEATURE:
<223> OTHER INFORMATION: PCR primer

<400> SEQUENCE: 72
caccagatct cttctgaagg cctttaatct tctc                                 34

<210> SEQ ID NO 73
<211> LENGTH: 40
<212> TYPE: DNA
<213> ORGANISM: Artificial Sequence
<220> FEATURE:
<223> OTHER INFORMATION: PCR primer

<400> SEQUENCE: 73
caccatggga tccgcttcta actttactca gttcgttctc                           40

<210> SEQ ID NO 74
<211> LENGTH: 28
<212> TYPE: DNA
<213> ORGANISM: Artificial Sequence
<220> FEATURE:
<223> OTHER INFORMATION: PCR primer

<400> SEQUENCE: 74
tatgagatct gtagatgccg gagttggc                                        28

<210> SEQ ID NO 75
<211> LENGTH: 32
<212> TYPE: DNA
<213> ORGANISM: Artificial Sequence
<220> FEATURE:
<223> OTHER INFORMATION: PCR primer

<400> SEQUENCE: 75
gacaccatgg gatccgcatt gacgcaagag cg                                   32

<210> SEQ ID NO 76
<211> LENGTH: 34
<212> TYPE: DNA
<213> ORGANISM: Artificial Sequence
<220> FEATURE:
```

<223> OTHER INFORMATION: PCR primer

<400> SEQUENCE: 76
tatgagatct tcgacgtaat ccaagtttct caac        34

<210> SEQ ID NO 77
<211> LENGTH: 18
<212> TYPE: DNA
<213> ORGANISM: Artificial Sequence
<220> FEATURE:
<223> OTHER INFORMATION: PCR primer

<400> SEQUENCE: 77
gaagcgcgat cacatggt        18

<210> SEQ ID NO 78
<211> LENGTH: 18
<212> TYPE: DNA
<213> ORGANISM: Artificial Sequence
<220> FEATURE:
<223> OTHER INFORMATION: PCR primer

<400> SEQUENCE: 78
ccatgccgag agtgatcc        18

<210> SEQ ID NO 79
<211> LENGTH: 20
<212> TYPE: DNA
<213> ORGANISM: Artificial Sequence
<220> FEATURE:
<223> OTHER INFORMATION: PCR primer

<400> SEQUENCE: 79
ggctacccgt gatattgctg        20

<210> SEQ ID NO 80
<211> LENGTH: 19
<212> TYPE: DNA
<213> ORGANISM: Artificial Sequence
<220> FEATURE:
<223> OTHER INFORMATION: PCR primer

<400> SEQUENCE: 80
gcgataccgt aaagcacga        19

<210> SEQ ID NO 81
<211> LENGTH: 736
<212> TYPE: DNA
<213> ORGANISM: Artificial Sequence
<220> FEATURE:
<223> OTHER INFORMATION: mutant ORF

<400> SEQUENCE: 81
atggcttcca aggtgtacga ccccgagcaa cgcaaacgca tgatcactgg gcctcagtgg        60
tgggctcgct gcaagcaaat gaacgtgctg gactccttca tcaactacta tgattccgag       120
aagcacgccg agaacgccgt gatttttctg catggtaacg ctgcctccag ctacctgtgg       180
aggcacgtcg tgcctcacat cgagcccgtg gctagatgca tcatccctga tctgatcgga       240
atgggtaagt ccggcaagag cgggaatggc tcatatcgcc tcctggatca ctacaagtac       300
ctcaccgctt ggttcgagct gctgaacctt ccaaagaaaa tcatctttgt gggccacgac       360 tgggggggctt gtctggcctt tcactactcc tacgagcacc aagacaagat caaggccatc       420
gtccatgctg agagtgtcgt ggacgtgatc gagtcctgag acgagtgacc tgacatcgag       480

```
gaggatatcg ccctgatcag tccagattgt ccgcaactac aacgcctacc ttcgggccag      540
cgacgatctg cctaagatgt tcatcgagtc cgaccctggg ttcttttcca acgctattgt      600
cgagggagct aagaagttcc ctaacaccga gttcgtgaag gtgaagggcc tccacttcag      660
ccaggaggac gctccagatg aaatgggtaa gtacatcaag agcttcgtgg agcgcgtgct      720
gaagaacgag cagtaa                                                     736
```

<210> SEQ ID NO 82
<211> LENGTH: 720
<212> TYPE: DNA
<213> ORGANISM: Artificial Sequence
<220> FEATURE:
<223> OTHER INFORMATION: mutant ORF

<400> SEQUENCE: 82

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctgacccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 83
<211> LENGTH: 259
<212> TYPE: DNA
<213> ORGANISM: Artificial Sequence
<220> FEATURE:
<223> OTHER INFORMATION: Chimeric mutant

<400> SEQUENCE: 83

```
gattcttctg acacaacagt ctcgaactta agctgcagaa gttggtcgtg aggcactggg      60
caggtaagta tcaaggttac aagacaggtt taaggagacc aatagaaact gggcttgtcg     120
agacagagaa gactcttgcg tttctgatag gcacctattg gtcttactga catccacttt     180
gcctttctct ccacaggtgt ccactcccag ttcaattaca gctcttaagg ctagagtact     240
taatacgact cactatagg                                                  259
```

<210> SEQ ID NO 84
<211> LENGTH: 62
<212> TYPE: RNA
<213> ORGANISM: artificial
<220> FEATURE:
<223> OTHER INFORMATION: Artificial Sequence

<400> SEQUENCE: 84

```
ucagauccgc uagcgcuacc ggacucagau cuggggcgug auccgaaagg ugacccggau      60
cc                                                                    62
```

TRANSLATIONAL CONTROL SYSTEM USING RNA-PROTEIN INTERACTION MOTIF

CROSS-REFERENCE TO RELATED APPLICATIONS

This application is a Divisional of U.S. application Ser. No. 14/415,009, which is the U.S. National Stage application of PCT/JP2013/069958, filed Jul. 16, 2013, which claims priority from U.S. provisional application 61/672,219, filed Jul. 16, 2012.

The instant application contains a Sequence Listing which has been submitted in ASCII format via EFS-WEB and is hereby incorporated by reference in its entirety. Said ASCII copy, created on Apr. 19, 2018, is named sequence.txt and is 34 KB.

TECHNICAL FIELD

The present invention relates to a translational control system using an RNA-protein interaction motif.

BACKGROUND ART

Introduction of multiple genes into cells and translation and expression of them are increasingly required for engineering and understanding biological systems. Small-molecule-responsive translational regulatory systems are widely known and have been used for expressing transgenes. Such a method is a technique to equally regulate expression of multiple genes.

Up to the present, quantitative regulation of the expression of a protein from an exogenous gene in a eukaryote largely depends on a transcription factor responsive to added small molecules such as tetracycline (Deans T L, Cantor C R, Collins J J (2007) A tunable genetic switch based on RNAi and repressor proteins for regulating gene expression in mammalian cells. Cell 130:363-372). The activity of the transcription factor is determined depending upon the concentration of added effector molecules. Such a combination of effector molecules and a transcription factor equally regulates transcription levels of multiple target genes in a cell. FIG. 16 is a conceptual diagram of such a conventional system.

Post-transcriptional regulation of a target gene in a mammalian cell has been also reported (Okano H et al. (2005) Function of RNA-binding protein Musashi-1 in stem cells. Exp Cell Res. 306: 349-356).

The present inventors designed a target mRNA containing a kink-turn RNA motif, that is, a binding RNA motif of an archaeal ribosomal protein, L7Ae protein, and reported a "translation OFF switch" system for strongly decreasing the translation of this mRNA (WO2009/066757). FIG. 15 illustrates the structure of the kink-turn RNA motif and a brief outline of the system. The system functions as an On-Off switch. However, the use is restricted for quantitative translational regulation.

SUMMARY OF INVENTION

Technical Problem

It is extremely significant to individually and independently regulate expression of multiple exogenous genes by using a single regulatory factor. Such a system has, however, not yet been reported. The present invention was accomplished for solving this problem. The present inventors have conceived translational regulation for an mRNA encoding a target gene performed by using an RNA motif of an RNA-protein complex-derived nucleotide sequence or a variant thereof and a protein specifically binding to the RNA motif. As a result, the present inventors have found that quantitative translational repression can be performed by inserting the RNA motif in an mRNA 5'-untranslated region (hereinafter abbreviated as 5'UTR) while altering the number of inserted RNA motifs and a distance of the insertion portion from the 5' terminus. Thus, the present invention was accomplished.

Solution to Problem

Specifically, according to one embodiment, the present invention provides a translational control method using an RNA-protein interaction motif, comprising a step of introducing an mRNA having: a 5'UTR regulation structure comprising (1) a cap structure at the 5' terminus, (2) a spacer positioned on the 3' side of the cap structure, and (3) one or more RNA motifs positioned on the 3' side of the spacer, which comprises an RNA-protein interaction motif-derived nucleotide sequence or a variant thereof; and a nucleotide sequence encoding a target protein gene on the 3' side of the 5'UTR regulation structure, into a cell in the presence of a protein specifically binding to the RNA motifs, wherein a translational level is decreased as the number of bases of the spacer decreases, and the translational level is decreased as the number of the RNA motifs increases.

According to another embodiment, the present invention provides an mRNA translational level decreasing method, comprising the step of providing, on the 5' side of a nucleotide sequence encoding a target protein gene, a 5'UTR regulation structure comprising
 (1) a cap structure at the 5' terminus,
 (2) a spacer positioned on the 3' side of the cap structure, and
 (3) one or more RNA motifs positioned on the 3' side of the spacer, which comprises an RNA-protein interaction motif-derived nucleotide sequence or a variant thereof, wherein translational level is decreased as the number of bases of the spacer decreases, and the translational level is decreased as the number of the RNA motifs increases.

According to still another embodiment, the present invention provides an mRNA comprising: a 5'UTR regulation structure comprising (1) a cap structure at the 5' terminus, (2) a spacer positioned on the 3' side of the cap structure, and (3) one or more RNA motifs positioned on the 3' side of the spacer, which comprises an RNA-protein interaction motif-derived nucleotide sequence or a variant thereof; and a nucleotide sequence encoding a target protein gene on the 3' side of the 5'UTR regulation structure, wherein translational level of the target protein is decreased in the presence of a protein specifically binding to the RNA motifs.

According to still another embodiment, the present invention provides a method for selecting an exogenous mRNA that translates a protein at a freely selected level in a cell, comprising the steps of (1) introducing the mRNA into a cell that expresses a protein specifically binding to a corresponding RNA motif; and (2) measuring a translational level of the protein to identify the mRNA providing a desired translational level.

According to still another embodiment, the present invention provides a method for regulating expression levels of target proteins from a plurality of different mRNAs encoding different target protein genes independently at different levels, comprising the steps of introducing a first mRNA, which has a cap structure at the 5' terminus, contains a nucleotide sequence encoding a first target protein gene, and has, on the 3' side of the cap structure and the 5' side of an initiation codon, a first regulation structure comprising a spacer and one or more first RNA motifs of an RNA-protein interaction motif-derived nucleotide sequence or a variant thereof, into a cell in the presence of a protein specifically binding to the first RNA motifs; and introducing a second mRNA, which has a cap structure at the 5' terminus, contains a nucleotide sequence encoding a second target protein gene, and has, on the 3' side of the cap structure and the 5' side of an initiation codon, a second regulation structure comprising a spacer, and one or more second RNA motifs of an RNA-protein interaction motif-derived nucleotide sequence or a variant thereof, into a cell in the presence of a protein specifically binding to the second RNA motifs, wherein the first regulation structure and the second regulation structure are different from each other in the number of bases of the spacer and/or the number of the RNA motifs, and the first RNA motif and the second RNA motif are the same as each other, or the first RNA motif and the second RNA motif are variants specifically binding to the same protein but having different dissociation constants for the same protein.

According to still another embodiment, the present invention provides a translational regulation method using an RNA-protein interaction motif, comprising the step of introducing an mRNA, which has a 5'UTR regulation structure comprising (1) a cap structure on the 5' terminus, (2) one or more RNA motifs positioned on the 3' side of the cap structure, of an RNA-protein interaction motif-derived nucleotide sequence or a variant thereof, and (3) an ON switch cassette positioned on the 3' side of the RNA motifs and having a sequence comprising (a) a bait open reading frame (a bait ORF), (b) intron and (c) an internal ribosome entry site (IRES); and a nucleotide sequence encoding a target protein gene on the 3' side of the 5'UTR regulation structure, into a cell, and starting translation of the target protein by a protein specifically binding to the RNA motifs, wherein the bait ORF is a sequence comprising a stop codon within 500 bases from the 3' terminus thereof.

According to still another embodiment, the present invention provides an mRNA, comprising a 5'UTR regulation structure comprising (1) a cap structure at the 5' terminus, (2) one or more RNA motifs positioned on the 3' side of the cap structure, of an RNA-protein interaction motif-derived nucleotide sequence or a variant thereof, and (3) an ON switch cassette positioned on the 3' side of the RNA motifs and having a sequence comprising (a) a bait open reading frame (a bait ORF), (b) intron and (c) an internal ribosome entry site (IRES); and a nucleotide sequence encoding a target protein gene on the 3' side of the 5'UTR regulation structure site and having a nucleotide sequence encoding a gene of a target protein, wherein the bait ORF is a sequence comprising a stop codon in more than 320 bases from the intron.

Advantageous Effects of Invention

According to the present invention, expression levels of different proteins from a plurality of different mRNAs can be controlled independently at different levels in the presence of one and the same active factor, and thus, quantitative translational regulation can be realized.

BRIEF DESCRIPTION OF DRAWINGS

FIG. 5(A) illustrates the structure of the K-loop RNA motif (SEQ ID NO:2). FIG. 5(B) illustrates the structure of the Kl2 motif (SEQ ID NO:3).

FIGS. 6(A), 6(B) and 6(C) are schematic diagrams of an mRNA having a 5'UTR regulation structure comprising multiple Kl motifs.

FIG. 7 is a graph illustrating a relationship, obtained in an mRNA having a 5'UTR regulation structure comprising a spacer and a Kl motif, among the number of Kl motifs, the length of the spacer (i.e., a distance of the Kl motif from the 5' terminus) and the translational efficiency.

FIG. 12(A) illustrates a secondary structure of an MS2 stem-loop motif, that is, an RNA motif to which the MS2 coat protein specifically binds (SEQ ID NO:4). FIG. 12(B) illustrates a secondary structure of an Fr15 motif, that is, an RNA motif to which the *Bacillus* ribosomal protein S15 binds (SEQ ID NO:5).

FIGS. 17(A) and 17(B) are conceptual diagrams of an ON switch cassette, wherein FIG. 17(A) illustrates that a bait ORF is translated but a gene following an IRES sequence is not translated in the absence of a trigger protein, and FIG. 17(B) illustrates that a bait ORF is not translated but a gene following the IRES sequence is translated owing to the function of a trigger protein in the presence of the trigger protein.

FIGS. 18(A), 18(B), 18(C) and 18(D) illustrate microphotographs of DsRed (expression of a trigger protein) and EGFP (translational object) in HeLa cells into which combinations each of a Kt motif or a dKt motif (negative control) and L7A or MS2 coat protein (negative control) as a trigger protein is introduced in the ON switch cassette, FIG. 18(E) is a graph illustrating a fluorescent ratio of EGFP to DsRed in each combination, and FIG. 18(F) is a graph illustrating mRNA level attained by each combination.

FIG. 19(A) is a graph illustrating fluorescent intensity of EGFP against a quantity ratio between mRNA plasmid and trigger protein plasmid in each combination of an ON switch cassette or an OFF switch cassette and a Kt motif or an Fr15 motif, FIG. 19(B) is a graph illustrating fluorescent intensity of EGFP against a dissociation constant (Kd) in each combination of the ON switch cassette or the OFF switch cassette and each of Kt motif variants, and FIGS. 19(C) and (D) shows the result of western blotting analysis for evaluating transcription activity of cognate (L7Ae and S15, respectively) and noncognate (MS2CP and L7KK, respectively) input proteins.

FIG. 20(A) is a conceptual diagram of a switch-inverting module with or without a premature termination codon (PTC) (ON or ONn) (shown in left), and a graph illustrating a fluorescent intensity of EGFP from switches inverted (shown in right), FIG. 20(B) shows the result of western blotting analysis after siRNA-induced knocking down of nonsense mutation-dependent mRNA decay mechanism (NMD) factors: SMG1, UPF1 and UPF2, wherein GAPDH was also analyzed as an internal control of the lysates, and FIG. 20(C) is a set of graphs illustrating the mean intensity of EGFP fluorescence in siRNA-treated cells introduced with each inverted switches (ON-Kt or ON-dKt) and trigger protein (MS2 or L7Ae).

FIG. 21(A) is a conceptual diagram of a series of switch-inverting modules modified in bait ORF (320 nt (ON32), 160 nt (ON16) or 80 nt (ON8), which means length between PTC and the spliced site) (shown in left) and a graph illustrating the mean intensity of EGFP fluorescence in the cells introduced with each inverted switches and trigger protein (shown in right), and FIG. 21(B) is a conceptual diagram of switch-inverting modules having a short chimeric intron (133 nt, ONc) and a graph illustrating the mean intensity of EGFP fluorescence in the cells introduced with the inverted switches (ONc-Kt or ONc-dKt) and trigger protein (MS2 or L7Ae).

DESCRIPTION OF EMBODIMENTS

Figure 1:
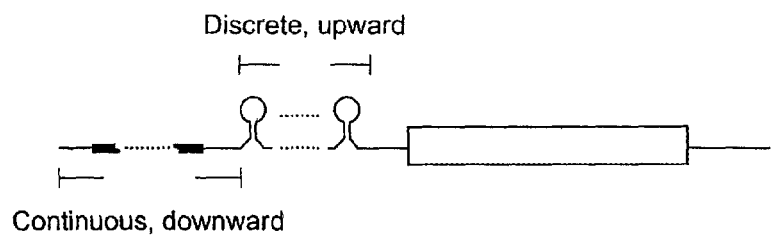
FIG. 1 is a conceptual diagram illustrating variability of an mRNA 5'UTR regulation structure capable of performing translational control for a target protein in accordance with the number of RNA motifs and the base length of a spacer.

The present invention will now be described in detail with reference to embodiments. It is noted that the present invention is not limited to the following embodiments.

According to a first embodiment, the present invention relates to a translational control method. The translational control method is carried out by using an mRNA having a regulation structure in the 5'UTR. The 5'UTR regulation structure contains a spacer positioned on the 3' side of a cap structure and on the 5' side of an initiation codon, and one or more RNA-protein interaction motif-derived nucleotide sequences positioned on the 3' side of the spacer and on the 5' side of the initiation codon. When the mRNA having the regulation structure in the 5'UTR is introduced into a cell in the presence of a protein specifically binding to the RNA-protein interaction motif-derived nucleotide sequence contained in the regulation structure, the translation of a protein encoded by the mRNA can be controlled depending upon the structural characteristics of the 5'UTR regulation structure. Herein, an RNA-protein interaction motif-derived nucleotide sequence or a variant thereof is referred to as an "RNA motif" Besides, a protein specifically binding to the RNA motif and functioning as an indispensable element in the translational regulation is also referred to as a "trigger protein."

First, the mRNA having the regulation structure in the 5'UTR will be described. The mRNA having the regulation structure in the 5'UTR of this embodiment is an artificially prepared non-natural mRNA that has a cap structure at the 5' terminus, has an initiation codon and is designed to encode a desired target protein gene, and this mRNA is translated in a eukaryote cell so that the target protein encoded by the mRNA can be expressed.

A structure on the 3' side of the initiation codon can be designed by those skilled in the art on the basis of the structure of a freely selected natural or non-natural known mRNA. Typically, the nucleotide sequence can be determined so as to have an initiation codon, an open reading frame and a poly A sequence in the 3'UTR.

In the mRNA having the regulation structure in the 5'UTR of the present embodiment, the 5'UTR contains, at the 5' terminus, 7-methylguanosine 5'-phosphate corresponding to the cap structure. This is because it is an indispensable structure in eukaryotic mRNA translation.

The 5'UTR regulation structure contains at least one or more RNA-protein interaction motif-derived nucleotide sequences or a variant thereof. In the present invention, an RNA-protein complex interaction motif-derived nucleotide sequence encompasses: a nucleotide sequence known as an RNA sequence in the RNA-protein interaction motif of a known natural RNA-protein complex; and a nucleotide sequence corresponding to an RNA sequence in an artificial RNA-protein complex interaction motif obtained by the in vitro evolution method. The RNA-protein complexes are assemblies of proteins and RNAs which are confirmed in vivo in large numbers, and are 3D objects having complicated structures.

A natural RNA-protein complex interaction motif-derived nucleotide sequence is usually composed of approximately 10 to 80 bases and is known to specifically bind to a particular amino acid sequence of a particular protein in a noncovalent manner, i.e., through a hydrogen bond. Such a natural RNA-protein complex interaction motif-derived nucleotide sequence can be selected from Tables 1 and 2 below and the database: http://gibk26.bse.kyutech.ac.jp/jouhou/image/dna-protein/rna/rna.html available on the website.

TABLE 1

| 0RNA | Protein | Kd | Reference |
|---|---|---|---|
| 5S RNA (*Xenopus laevis* oocyte) | 5R1 | 0.64 ± 0.10 nM | Nat Struct Biol. 1998 Jul; 5(7): 543-6 |
| 5S RNA (*Xenopus laevis* oocyte) | 5R2 | 0.35 ± 0.03 nM | Nat Struct Biol. 1998 Jul; 5(7): 543-6 |
| dsRNA | B2 | 1.4 ± 0.13 nM | Nat Struct Mol Biol. 2005 Nov; 12(11): 952-7 |
| RNA splicing motif with UGCAUGU element | Fox-1 | 0.49 nM at 150 mM salt | EMBO J. 2006 Jan 11; 25(1): 163-73. |
| TGE | GLD-1 | 9.2 ± 2 nM | J Mol Biol. 2005 Feb 11; 346(1): 91-104. |
| sodB mRNA | Hfq | 1.8 nM | EMBO J. 2004 Jan 28; 23(2): 396-405. |
| RyhB (siRNA) | Hfq | 1500 nM | Annu Rev Microbiol. 2004; 58: 303-28 |
| mRNA | HuD | 0.7 ± 0.02 nM | Nat Struct Biol. 2001 Feb; 8(2): 141-5 |
| S domain of 7S RNA | human SRP19 | | RNA. 2005 Jul; 11(7): 1043-50. Epub 2005 May 31 |
| Large subunit of SRP RNA | human SRP19 | 2 nM | Nat Struct Biol. 2001 Jun; 8(6): 515-20 |
| 23S rRNA | L1 | | Nat Struct Biol. 2003 Feb; 10(2): 104-8 |
| 23S rRNA | L11 | | Nat Struct Biol. 2000 Oct; 7(10): 834-7 |
| 5S rRNA | L18 | | Biochem J. 2002 May 1; 363(Pt 3): 553-61 |
| 23S rRNA | L20 | 13 ± 2 nM | J Biol Chem. 2003 Sep 19; 278(38): 36522-30. |
| Own mRNA site1 | L20 | 88 ± 23 nM | J Biol Chem. 2003 Sep 19; 278(38): 36522-30. |
| Own mRNA site2 | L20 | 63 ± 23 nM | Mol Microbiol. 2005 Jun; 56(6): 1441-56 |
| 23S rRNA | L23 | | J Biomol NMR. 2003 Jun; 26(2): 131-7 |
| 5S rRNA | L25 | | EMBO J. 1999 Nov 15; 18(22): 6508-21 |
| Own mRNA | L30 | | Nat Struct Biol. 1999 Dec; 6(12): 1081-3. |
| mRNA | LicT | | EMBO J. 2002 Apr 15; 21(8): 1987-97 |
| Own mRNA | MS2 coat | 39 ± 5 nM | FEBS J. 2006 Apr; 273(7): 1463-75 |
| Stem-loop RNA motif | Nova-2 | | Cell. 2000 Feb 4; 100(3): 323-32 |
| SL2 | Nucleocapsid | 110 ± 50 nM | J Mol Biol. 2000 Aug 11; 301(2): 491-511 |
| Pre-rRNA | Nucleolin | | EMBO J. 2000 Dec 15; 19(24): 6870-81 |
| | p19 | 0.17 ± 0.02 nM | Cell. 2003 Dec 26; 115(7): 799-811 |
| Box C/D | L7Ae | 0.9 ± 0.2 nM | RNA. 2005 Aug; 11(8): 1192-200. |

TABLE 2

| RNA | Protein | Kd | Reference |
|---|---|---|---|
| siRNA with the characteristic two-base 3' overhangs | PAZ (PiWi Argonaut and Zwille) | | Nat Struct Biol. 2003 Dec; 10(12): 1026-32. |
| dsRNA | Rnase III | | Cell. 2006 Jan 27; 124(2): 355-66 |
| HIV-1 RRE (IIB) | RR1-38 | 3-8 nM | Nat Struct Biol. 1998 Jul; 5(7): 543-6 |
| Own mRNA | S15 | 5 nM | EMBO J. 2003 Apr 15; 22(8): 1898-908 |
| 16S rRNA | S15 | 6 nM | Nat Struct Biol. 2000 Apr; 7(4): 273-277. |
| Own mRNA | S15 | 43 nM | EMBO J. 2003 Apr 15; 22(8): 1898-908 |
| 16S rRNA | S4 | 6.5 µM in 4° C., 1.7 nM in 42° C. | J Biol Chem. 1979 Mar 25; 254(6): 1775-7 |
| 16S rRNA | S4 | 18 µM | J Biol Chem. 1979 Mar 25; 254(6): 1775-7 |
| 16S rRNA | S8 | 26 ± 7 nM | J Mol Biol. 2001 Aug 10; 311(2): 311-24 |
| mRNA | S8 | 200 nM | RNA. 2004 Jun; 10(6): 954-64 |
| mRNA | SacY | 1400 nM | EMBO J. 1997 Aug 15; 16(16): 5019-29 |
| SnRNA | Sm | | Cold Spring Harb Symp Quant Biol. 2006; 71: 313-20. |

TABLE 2-continued

| RNA | Protein | Kd | Reference |
|---|---|---|---|
| tmRNA | SmpB | 21 ± 7 nM | J Biochem (Tokyo). 2005 Dec; 138(6): 729-39 |
| TD3 of tmRNA | SmpB | 650 nM | J Biochem (Tokyo). 2005 Dec; 138(6): 729-39 |
| U1 snRNA | snRNP U1A | 0.032 ± 0.007 nM (salt dependence) | Nat Struct Biol. 2000 Oct; 7(10): 834-7 |
| S domain of 7S RNA | SRP54 | 500 nM | RNA. 2005 Jul; 11(7): 1043-50. |
| TAR | Tat | 200-800 nM | Nucleic Acids Res. 1996 Oct 15; 24(20): 3974-81 |
| BIV TAR | Tat | 1.3 nM or 8 nM or 60 nM (Mg dependence) | Mol Cell. 2000 Nov; 6(5): 1067-76 |
| tRNA$^{Thr}$ | ThrRS | 500 nM | Nat Struct Biol. 2002 May; 9(5): 343-7 |
| thrS mRNA operator | ThrRS | 10 nM | Trends Genet. 2003 Mar; 19(3): 155-61 |
| Single stranded mRNA | TIS11d | | Nat Struct Mol Biol. 2004 Mar; 11(3): 257-64. |
| PSTVd | Virp1 | 500 nM | Nucleic Acids Res. 2003 Oct 1; 31(19): 5534-43 |
| RNA hairpin; Smaug recognition element (SRE) | Vts1p | 30 nM | Nat Struct Mol Biol. 2006 Feb; 13(2): 177-8. |
| λ BoxB | λ N | 90 nM | Cell. 1998 Apr 17; 93(2): 289-99 |

An artificial RNA-protein complex interaction motif-derived nucleotide sequence is the nucleotide sequence of an RNA in an RNA-protein interaction motif of an artificially designed RNA-protein complex. Such a nucleotide sequence is usually composed of approximately 10 to 80 bases and is designed to specifically bind to a particular amino acid sequence of a particular protein in a noncovalent manner, i.e., through a hydrogen bond. An example of such an artificial RNA-protein complex interaction motif-derived nucleotide sequence includes an RNA aptamer specifically binding to a particular protein. An RNA aptamer specifically binding to a desired target protein can be obtained by, for example, an evolutionary engineering method known as the in vitro selection method or the SELEX method. A trigger protein used in this case is a protein to which the RNA aptamer binds. For example, nucleotide sequences listed in Table 3 below are known, and these nucleotide sequences may be also used as the RNA-protein complex interaction motif-derived nucleotide sequence of the present invention.

TABLE 3

| RNA | Protein | Kd | Reference |
|---|---|---|---|
| Rev aptamer 5 | Rev | 190 nM | RNA. 2005 Dec; 11(12): 1848-57 |
| Aptamer | p50 | 5.4 ± 2.2 nM | Proc Natl Acad Sci USA. 2003 Aug 5; 100(16): 9268-73. |
| BMV Gag aptamer | BMV Gag | 20 nM | RNA. 2005 Dec; 11(12): 1848-57 |
| BMV Gag aptamer | CCMV Gag | 260 nM | RNA. 2005 Dec; 11(12): 1848-57 |
| CCMV Gag aptamer | CCMV Gag | 280 nM | RNA. 2005 Dec; 11(12): 1848-57 |
| CCMV Gag aptamer | BMV Gag | 480 nM | RNA. 2005 Dec; 11(12): 1848-57 |

In the present embodiment, as for the RNA-protein complex interaction motif-derived nucleotide sequence, an RNA-protein complex corresponding to the origin of the nucleotide sequence preferably has a dissociation constant Kd of approximately 0.1 nM to approximately 1 μM.

Furthermore, in addition to the RNA-protein complex interaction motif-derived nucleotide sequence itself, a variant of such a sequence is also encompassed by the RNA motif of the present invention. In the present invention, a variant refers to a variant having a dissociation constant Kd not less than 10%, 20%, 30%, 40% or 50% or not more than 10%, 20%, 30%, 40% or 50% from a protein specifically binding to the RNA-protein interaction motif-derived nucleotide sequence. Such a variant can be appropriately selected and used so as to attain a desired translational level of the mRNA containing the RNA-protein complex interaction motif. Here, attention should be paid to the fact that translational efficiency from an mRNA having a motif with a higher dissociation constant Kd is increased and the translational efficiency decreases as the dissociation constant Kd decreases. Furthermore, the nucleotide sequence of such a variant may be one that can be hybridized, under stringent conditions, to a nucleic acid (corresponding to a complementary strand) having a complementary sequence with the RNA-protein interaction motif-derived nucleotide sequence (corresponding to a positive strand). Here, the stringent conditions can be determined on the basis of a melting temperature (Tm) of the nucleic acid to be bound as is taught by Berger and Kimmel (1987, Guide to Molecular Cloning Techniques, Methods in Enzymology, Vol. 152, Academic Press, San Diego Calif.). For example, as conditions for washing after hybridization, conditions of about "1×SSC, 0.1% SDS and 37° C." can be generally employed. The complementary strand is preferably retained to be hybridized to the corresponding positive strand even when it is washed under such conditions. Although not particularly limited, as more stringent hybridization conditions, the hybridized state between the positive strand and the complementary strand can be retained under washing conditions about "0.5×SSC, 0.1% SDS and 42° C.", and even more stringent, under conditions about "0.1×SSC, 0.1% SDS and 65° C.". Specifically, the variant has a nucleotide sequence with sequence identity of at least 90%, preferably, at least 95%, 96%, 97%, 98% or 99% with the RNA-protein interaction motif-derived nucleotide sequence. Such a variant can maintain a constant binding with the protein specifically binding to the RNA-protein interaction motif-derived nucleotide sequence, so as to make a contribution to translational repression.

Specific examples of the RNA motif of the present embodiment include 5'-GGGCGUGAUGC-GAAAGCUGACCC-3' (SEQ ID NO: 1), that is, a nucleotide sequence to which L7Ae is known to be related to RNA modification such as RNA methylation or pseudouridylation (Moore T et. al., Structure Vol. 12, pp. 807-818 (2004)) binds, and its variants, kink-loop (SEQ ID NO: 2) and kink-loop2 (SEQ ID NO: 3).

Other specific examples include MS2 stem-loop motif, that is, an RNA motif to which an MS2 coat protein specifically binds (22: Keryer-Bibens C, Barreau C, Osborne H B (2008) Tethering of proteins to RNAs by bacteriophage proteins. Biol Cell 100: 125-138) (SEQ ID NO: 4), and Fr15, that is, an RNA motif to which *Bacillus* ribosomal protein S15 binds (24: Batey R T, Williamson J R (1996) Interaction of the *Bacillus stearothermophilus* ribosomal protein S15 with 16 S rRNA: I. Defining the minimal RNA site. J Mol Biol 261: 536-549) (SEQ ID NO: 5).

Still other specific examples include 5'-GGCGUAU-GUGAUCUUUCGUGUGGGUCACCACUGCGCC-3' (SEQ ID NO: 6), that is, a nucleotide sequence to which threonyl-tRNA synthetase, an enzyme for aminoacylation, binding to its own mRNA and known to have a feedback inhibition function to inhibit translation binds (Cell (Cambridge, Mass.) v97, pp. 371-381 (1999)), and a variant thereof. Still other specific examples include R9-2;5'-GGGUGCUUCGAGCGUAGGAAGAAAGC-CGGGGGCUGCAGAUAAUGUAUAGC-3' (SEQ ID NO: 7), that is, an RNA-protein complex interaction motif-derived nucleotide sequence derived from Bcl-2 family CED-9, a cancer cell-specific intrinsic protein, a variant thereof, a nucleotide sequence derived from an aptamer of an RNA sequence binding to NF-kappa B and a variant thereof.

In the present embodiment, the spacer contained in the 5'UTR regulation structure if necessary is a portion composed of one or more bases and is positioned between the cap structure at the 5' terminus and the RNA motif. The nucleotide sequence of the spacer is not particularly limited but may be a freely chosen sequence, and is preferably a nucleotide sequence that does not form a particular secondary or tertiary structure, specifically, a nucleotide sequence that does not include an initiation codon and does not encode a particular gene. In the present embodiment, the spacer may be omitted, and hereinafter, a case in which the spacer is omitted is described as a case in which the number of bases of the spacer is 0.

In the present embodiment, the 5'UTR of the mRNA contains the cap structure, the spacer and the RNA motif arranged in this order from the 5' terminus. FIG. 1 is a conceptual diagram of the 5'UTR regulation structure with the cap structure omitted.

The spacer is placed immediately 3' to the cap structure. Herein, "immediately" means that there is no base between the cap structure and the spacer, but 1 to 6 technically necessary bases, such as a restriction enzyme site, may be placed therebetween in some cases.

The length of the spacer may be a freely chosen number of bases in accordance with desired level of translation of mRNA, and the spacer may have, for example, 0 to 1000 bases, 0 to 900 bases, 0 to 800 bases, 0 to 700 bases, 0 to 600 bases, 0 to 500 bases, 0 to 450 bases, 0 to 400 bases, 0 to 350 bases, 0 to 300 bases, 0 to 250 bases, 0 to 200 bases, 0 to 150 bases, 0 to 100 bases, 0 to 50 bases, 0 to 40 bases, 0 to 30 bases, 0 to 20 bases or 0 to 10 bases, and preferably has 0 to 350 bases. A nucleotide sequence indispensable in the embodiment, such as a restriction enzyme site, may be regarded as a part of the nucleotide sequence of the spacer. A spacer having a smaller number of bases shows a larger translational repression effect, so as to obtain an mRNA with lower translational efficiency. By increasing/decreasing the number of bases of the spacer, an mRNA having translational efficiency substantially continuously regulated can be designed.

Examples of the spacer include sequences listed in Table 4.

TABLE 4

| Base length | Sequences | SEQ ID NO. |
|---|---|---|
| 18 | UCAGAUCCGCUAGGAUCU | 8 |
| 32 | UCAGAUCCGCUAGCGCUACCGGACUCAGAUCU | 9 |
| 51 | UCAGAUCCGCUAGCCGCCUGUUUUGACCGCUGGGAUCUGCCAUUGAGAUCU | 10 |
| 67 | UCAGAUCCGCUAGCCCGACCGCCUUACUGCCGCCUGUUUUGACCGCUGGGAUCUGCCAUUGAGAUCU | 11 |
| 94 | UCAGAUCCGCUAGCUCGGAUUAGGGCCGCAAGAAAACUAUCCCGACCGCCUUACUGCCGCCUGUUUUGACCGCUGGGAUCUGCCAUUGAGAUCU | 12 |
| 120 | UCAGAUCCGCUAGCGCAGGUAGCAGAGCGGGUAAACUGGCUCGGAUUAGGGCCGCAAGAAAACUAUCCCGACCGCCUUACUGCCGCCUGUUUUGACCGCUGGGAUCUGCCAUUGAGAUCU | 13 |
| 145 | UCAGAUCCGCUAGCGGAUUGGCCUGAACUGCCAGCUGGCGCAGGUAGCAGAGCGGGUAAACUGGCUCGGAUUAGGGCCGCAAGAAAACUAUCCCGACCGCCUUACUGCCGCCUGUUUUGACCGCUGGGAUCUGCCAUUGAGAUCU | 14 |
| 164 | UCAGAUCCGCUAGCGAUACACCGCAUCCGGCGCGGAUUGGCCUGAACUGCCAGCUGGCGCAGGUAGCAGAGCGGGUAAACUGGCUCGGAUUAGGGCCGCAAGAAAACUAUCCCGACCGCCUUACUGCCGCCUGUUUUGACCGCUGGGAUCUGCCAUUGAGAUCU | 15 |
| 320 | UCAGAUCCGCUAGCGAUACACCGCAUCCGGCGCGGAUUGGCCUGAACUGCCAGCUGGCGCAGGUAGCAGAGCGGGUAAACUGGCUCGGAUUAGGGCCGCAAGAAAACUAUCCCGACCGCCUUACUGCCGCCUGUUUUGACCGCUGGGAUCUGCCAUUGAGAUCCGAUCCCGUCGUUUUACAACGUCGUGACUGGGAAAACCCUGGCGUUACCCAACUUAAUCGCCUUGCAGCACAUCCCCCUUUCGCCAGCUGGCGUAAUAGCGAAGAGGCCCGCACCGAUCGCCCUUCCCAACAGUUGCGCAGCCUGACCGGUAGAUCU | 16 |

The one or more RNA motifs are placed immediately 3' of the spacer. Also, "immediately" refers to a case in which 1 to 6 bases may be placed between the spacer and the RNA motif, but a nucleotide sequence provided between the spacer and the RNA motif is preferably regarded as a part of the spacer. If the 5'UTR regulation structure contains a plurality of RNA motifs, one RNA motif may "immediately" follow an adjacent RNA motif. Furthermore, it is preferable to design it so that a sequence of approximately 1 to 6 bases may be present as, for example, a restriction enzyme site between the RNA motif positioned closest to the 3' terminus and the initiation codon. The structure can be designed so as to insert a freely chosen number of RNA motifs on the 3' side of the spacer. For example, the number of RNA motifs may be 1 to 8, or particularly 1 to 4, but the number of RNA motifs is not limited to such a particular number.

As the number of inserted RNA motifs increases, the translational repression effect for the target protein encoded by the mRNA increases, and hence, the translational efficiency decreases. Accordingly, the mRNA translational efficiency is decreased, on the order of an mRNA having a 5'UTR regulation structure comprising one RNA motif, an mRNA having a 5'UTR regulation structure comprising two RNA motifs, an mRNA having a 5'UTR regulation structure comprising three RNA motifs and an mRNA having a 5'UTR regulation structure comprising four RNA motifs, as long as the rest of the 5'UTR structure is the same.

In the 5'UTR regulation structure, the translational efficiency can be regulated mainly depending upon the number of RNA motifs. This translational efficiency is discretely regulated by increasing or decreasing the number of RNA motifs. The number of RNA motifs is, for example, 1 to 20, preferably 1 or more or 2 or more, and 20 or less, 10 or less, 9 or less, 8 or less, 7 or less, 6 or less, 5 or less, or 4 or less.

As described above, the total base length of the 5'UTR of the mRNA of the present invention is determined depending upon the length of the spacer and the number of RNA motifs. However, it is not preferable that the 5'UTR of the mRNA of the present embodiment form a complicated tertiary structure in the whole region. This is because the translational regulation is made to function when a trigger protein binds to the RNA motif, and hence, if a tertiary structure to which a trigger protein cannot bind is formed, there is a possibility that the regulation function cannot be secured. The possibility of the 5'UTR of a designed mRNA forming a complicated tertiary structure can be calculated by using, on a computer, appropriate software, such as Discovery Studio or Centrolid Fold. Then, the mRNA can be designed so as to prevent the 5'UTR from forming such a complicated tertiary structure. Alternatively, after actually preparing an mRNA, binding between the mRNA and a trigger protein may be confirmed in vitro, or translation obtained in the absence of a trigger protein may be confirmed in a cell, so as to confirm whether or not the designed structure is a structure in which the translational regulation cannot work because the trigger protein cannot bind thereto.

In the mRNA having the regulation structure in the 5'UTR of the present embodiment, the translation is decreased and the translational efficiency is lower in the presence of a trigger protein as compared with an mRNA encoding the same gene but having no regulation structure in the 5'UTR. On the other hand, in the of absence of the trigger protein, the translational efficiency is substantially equivalent in the mRNA having the regulation structure in the 5'UTR and the mRNA encoding the same gene but having no regulation structure in the 5'UTR. When mRNAs have different sequences in the 5'UTR regulation structure, the translational efficiency is generally different. These characteristics of mRNAs may be used for designing, for example, an mRNA capable of achieving translational efficiency with a freely chosen value ranging between approximately 0% and approximately 99% in the presence of a trigger protein as compared with an mRNA having no regulation structure in the 5'UTR. The relationship among the translational efficiency, the number of bases of the spacer and the number of RNA motifs can be determined, for example, on the basis of a standard curve obtained by designing and preparing a plurality of mRNAs having different 5'UTR regulation structures and measuring translational efficiency of these mRNAs. The translational regulation can be accurately performed by designing the structure of the 5'UTR by appropriately using the number of bases of the spacer for achieving the aforementioned continuous regulation and the number of RNA motifs for achieving the discrete regulation.

In another embodiment, since the translational efficiency is determined depending upon the number of bases of the spacer and the type and the number of RNA motifs, mRNAs having 5'UTRs containing a large number of regulation structures are prepared by combining these variable elements. A combination achieving desired translational efficiency is selected from the employed combinations, so that an mRNA having a regulation structure in the 5'UTR and realizing desired translational efficiency can be obtained.

When a freely chosen mRNA having a regulation structure in the 5'UTR can be designed and its nucleotide sequence can be determined, those skilled in the art can prepare such an mRNA by any of a plurality of conventional gene engineering methods. An example of the methods includes a method in which an mRNA is expressed in a cell by using an expression vector. This method can be performed by introducing, into a cell, an expression vector having a sequence in which a promoter capable of functioning in a host cell and an mRNA having a regulation structure in the 5'UTR are functionally concatenated. As the expression vector, for example, virus vectors such as a retrovirus, lentivirus, adenovirus, adeno-associated virus, herpes virus and Sendai virus vectors, or animal cell expression plasmids (such as pA1-11, pXT1, pRc/CMV, pRc/RSV and pcDNAI/Neo) can be used. Furthermore, as the promoter, an EF-α promoter, a CAG promoter, an SRα promoter, an SV40 promoter, an LTR promoter, a CMV (cytomegalovirus) promoter, an RSV (Rous sarcoma virus) promoter, an MoMuLV (Moloney murine leukemia virus) LTR, an HSV-TK (Herpes simplex virus thymidine kinase) promoter or the like can be used. Especially, an EF-α promoter, a CAG promoter, an LTR and a CMV promoter can be suitably used. Furthermore, the expression vector may appropriately contain an enhancer, a selectable marker gene, SV40 replication origin and the like. Examples of the selectable marker gene include a dihydrofolate reductase gene, a hygromycin resistance gene, a Blasticidin resistance gene, a neomycin resistance gene and a puromycin resistance gene. As other exemplary methods, if the mRNA is directly introduced into a cell without using an expression vector, the mRNA can be introduced into a cell by a lipofection method, a liposomal method, an electroporation method, a calcium phosphate transfection method, a DEAE dextran method, a microinjection method, a gene gun method or the like. An mRNA can be synthesized from a template DNA having a desired mRNA sequence by the RNA polymerase method, and the synthesized RNA is provided, at the 5' terminus, with a cap structure by using, for example, m7G cap analogue (Promega), so as to be used as the mRNA of the present embodiment.

A translational regulation method for a target protein in a cell by using the thus prepared mRNA may be performed by following method. The described mRNA having the regulation structure in the 5'UTR plays a functional role in the presence of the trigger protein specifically binding to the RNA motif contained in the regulation structure. In this method, it is necessary to introduce, into a cell, the mRNA having the regulation structure in the 5'UTR and the protein specifically binding to the RNA motif contained in this regulation structure. Accordingly, in one embodiment, the method for regulating translation of a protein in a cell comprises a step of introducing, into a cell, an mRNA having a regulation structure in the 5'UTR and a protein specifically binding to an RNA motif contained in the regulation structure.

The step of introducing the mRNA having the regulation structure in the 5'UTR into a cell can be carried out by introducing an expression vector for expressing the mRNA or the mRNA itself by any of the aforementioned methods. The amount introduced is varied depending on the cell for introduction, the introducing method and the type of introduction reagent, and those skilled in the art can appropriately select them for attaining a desired translational level.

The trigger protein is determined in accordance with the RNA motif. Such a trigger protein is not particularly limited, and examples of the protein include those listed in Tables 1 to 3. The trigger protein is preferably a protein intrinsically expressed in a cell of interest. The trigger protein may be a fusion protein fused with another protein having a different function as long as it contains a protein specifically binding to the RNA motif contained in the 5'UTR regulation structure. The step of introducing the trigger protein into a cell can be carried out by introducing, into a cell, an expression vector having a gene encoding the protein or the protein fused with a protein transduction domain (PTD) or a cell penetrating peptide (CPP). Examples of the PTD include drosophila-derived AntP, HIV-derived TAT (Frankel, A. et al., Cell 55, 1189-93 (1988) or Green, M. & Loewenstein, P. M. Cell 55, 1179-88 (1988)), Penetratin (Derossi, D. et al., J. Biol. Chem. 269, 10444-50 (1994)), Buforin II (Park, C. B. et al., Proc. Natl Acad. Sci. USA 97, 8245-50 (2000)), Transportan (Pooga, M. et al., FASEB J. 12, 67-77 (1998)), MAP (model amphipathic peptide) (Oehlke, J. et al., Biochim. Biophys. Acta. 1414, 127-39 (1998)), K-FGF (Lin, Y. Z. et al., J. Biol. Chem. 270, 14255-14258 (1995)), Ku70 (Sawada, M. et al., Nature Cell Biol. 5, 352-7 (2003)), Prion (Lundberg, P. et al., Biochem. Biophys. Res. Commun. 299, 85-90 (2002)), pVEC (Elmquist, A. et al., Exp. Cell Res. 269, 237-44 (2001)), Pep-1 (Morris, M. C. et al., Nature Biotechnol. 19, 1173-6 (2001)), Pep-7 (Gao, C. et al., Bioorg. Med. Chem. 10, 4057-65 (2002)), SynB1 (Rousselle, C. et al., Mol. Pharmacol. 57, 679-86 (2000)), HN-I (Hong, F. D. & Clayman, G L. Cancer Res. 60, 6551-6 (2000)), and one using a cell penetrating domain of a protein such as HSV-derived VP22. An example of the CPP includes polyarginine such as 11R (Cell Stem Cell, 4, 381-384 (2009)) or 9R (Cell Stem Cell, 4, 472-476 (2009)). In order to increase/decrease the amount of trigger protein expressed in the cell, the number of plasmid vectors to be introduced can be altered, so that the translation of the mRNA having the regulation structure in the 5'UTR can be further controlled. Although not particularly limited, the plasmid vector expressing the trigger protein can be introduced into the cell so that a ratio between the mRNA having the regulation structure in the 5'UTR and the trigger protein can be, for example, 1:1, 2:1, 3:1, 4:1, 5:1, 6:1, 7:1, 8:1, 9:1, 10:1, 1:2, 1:3, 1:4, 1:5, 1:6, 1:7, 1:8, 1:9 or 1:10.

In the present invention, if an ON switch cassette is placed on the 5' side of an initiation codon of an mRNA gene and on the 3' side of an RNA motif, the translational repression can be reversed so as to control the mRNA translation to be carried out merely in the presence of a trigger protein. An ON switch cassette is composed of a sequence comprising, from the 5' side, a variant open reading frame (a bait ORF), intron and an internal ribosome entry site (IRES) in this order. A bait ORF is a variant ORF having, in a sequence encoding a freely chosen gene, a stop codon in more than 320 bases from the 3' end binding to intron for causing RNA decay by nonsense mutation-dependent mRNA decay mechanism (NMD). In the present invention the bait ORF may be any cording gene. An example of the bait ORF includes, but is not especially limited to, a sequence in which a stop codon is inserted at the 457th and/or 466th base from the 5' side of Renilla luciferase (SEQ ID NO: 17 or 81) or a sequence in which a stop codon is inserted at the 172th base from the 5' side of EGFP (SEQ ID NO: 82). Furthermore, the intron may have a sequence to which spliceosome binds, and an example includes a sequence of 20 or more bases containing a GT sequence on the 5' end and an AG sequence on the 3' end. Preferably, the intron is human β globin intron (SEQ ID NO: 18) or chimeric intron (SEQ ID NO: 83).

Such an mRNA having the 5'UTR regulation structure comprising the ON switch cassette can be introduced into a cell, so that the translation of the target protein can be started by the trigger protein. Furthermore, the level of translation can be regulated by appropriately controlling the spacer and the number of RNA motifs in the 5'UTR regulation structure as described above.

In one embodiment of the present invention, the translational regulation for multiple mRNAs different in the 5'UTR regulation structure and in the target protein to encode can be simultaneously carried out in the presence of a single trigger protein. In this translational regulation method, multiple mRNAs each having a different 5'UTR regulation structure and having a different target protein gene are first designed. A case of simultaneous translational regulation for two mRNAs will be exemplarily described, but simultaneous translational regulation for three, four, five or more mRNAs can be performed. Such simultaneous translational regulation can be carried out by designing and preparing multiple mRNAs by a design method similar to that described below and introducing the resulting mRNAs into a cell.

The first mRNA to be designed may have a nucleotide sequence having a cap structure at the 5' terminus and encoding a first target protein gene. A first 5'UTR regulation structure of the first mRNA is designed to contain a spacer of 0 to 350 bases and one or more first RNA motifs having an RNA-protein interaction motif-derived nucleotide sequence or a variant thereof. The second mRNA similarly having a nucleotide sequence having a cap structure at the 5' terminus and encoding a second target protein gene, and a second 5'UTR regulation structure of the second mRNA is also designed to contain a spacer of 0 to 350 bases and one or more second RNA motifs having an RNA-protein interaction motif-derived nucleotide sequence or a variant thereof. Thereafter, these two mRNAs are simultaneously introduced into a cell, so that the first target protein gene and the second target protein gene can be obtained as different genes desired to be expressed.

Preparation of an induced pluripotent stem cell (an iPS cell) by introducing four protein genes into a somatic cell will be exemplarily described according to Papapetrou E P et al. (2009) Stoichiometric and temporal requirements of Oct4, Sox2, Klf4, and c-Myc expression for efficient human iPSC induction and differentiation. Proc Natl Acad Sci USA 106: 12759-12764. A gene encoding Oct3/4 protein is used as a first target protein gene, a gene encoding Sox2 protein is used as a second target protein gene, a gene encoding Klf4 protein is used as a first target protein gene and a gene encoding c-Myc protein is used as a first target protein gene. These genes are designed so that the level of translation of the Oct3/4 protein can be about three times as high as that of the other three proteins by the method described above, and the thus designed genes are introduced into a somatic cell. In this manner, the preparation efficiency for the iPS cell can be advantageously increased.

The first RNA motif and the second RNA motif may be the same. Alternatively, the first RNA motif and the second RNA motif may be in a variant relationship in which they specifically bind to the same trigger protein but have different dissociation constants. This is because the translational regulation should function in the presence of a single trigger protein.

The numbers of the first RNA motifs and the second RNA motifs may be the same or different, and the numbers and the types of sequences of the spacers may be the same or different. The first 5'UTR regulation structure and the first 5'UTR regulation structure, however, should have different structures as a whole for achieving different translational efficiencies. The 5'UTR regulation structures for attaining desired translational efficiency can be appropriately designed by those skilled in the art by following the disclosure of the present application.

When the first mRNA and the second mRNA are designed, they are prepared by an ordinary method, and the prepared mRNAs are introduced into a cell expressing a trigger protein or introduced simultaneously with a trigger protein or genes expressing thereof into the same cell. In this manner, the translational regulation method can be carried out.

In the conventional technique, the expression level of an exogenous gene is regulated by controlling the type and the introduction amount of a promoter. When the present embodiment is employed, however, an exogenous gene can be stably expressed in a cell at a desired level of translation. Therefore, in the field of, for example, reprogramming techniques for expressing exogenous genes in cells in which optimum expression level of a gene is demanded, optimum cell transformation can be advantageously achieved through the reprogramming by regulating desired gene expression level in multiple stages.

In another embodiment, the present invention provides a method for selecting an exogenous mRNA translating a protein in a cell at a freely selected level. This method comprises the steps of (1) introducing any one of the aforementioned mRNAs having the 5'UTR regulation structures into a cell expressing a protein specifically binding to a corresponding RNA motif; and (2) measuring the level of translation of the protein to identify the mRNA achieving a desired translational level.

The step (1) can be performed, as described in the first embodiment, by designing any one of the mRNAs having the 5'UTR regulation structures and introducing the mRNA into a cell with an expression vector used or directly into a cell without using an expression vector. All of the description exemplarily given in the first embodiment is applicable also in this embodiment.

The step (2) can be performed by measuring the amount of the protein translated by the mRNA. The measurement of the amount of protein can be carried out by labeling the protein with an antibody to the desired protein or, if the protein to be translated is a fluorescent protein, by using the fluorescence, by a method known to those skilled in the art, such as ELISA (enzyme-linked immunosorbent assay), EIA (enzyme immunoassay), RIA (radioimmunoassay), Western blotting or flow cytometry.

The present invention will now be described in more details with reference to examples. It is noted that the present invention is not limited to the following examples.

EXAMPLE 1

[Measurement of Translational Efficiency of Sp-Kt-EGFP, Kt-Sp-EGFP and Kt-EGFP]

Figure 2A:
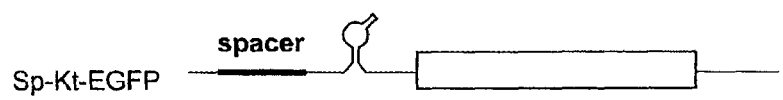
FIGS. 2(A) and 2(B) are schematic diagrams of an mRNA having a 5'UTR regulation structure comprising a spacer and one Kt motif.
Figure 2B:

Three mRNAs encoding the gene of EGFP were designed by providing, in the 5'UTR, a kink-turn RNA motif, that is, a binding RNA motif of an archaeal ribosomal protein, L7Ae protein. The kink-turn RNA motif is hereinafter referred to as the Kt motif FIGS. 2(A) and 2(B) illustrate the outline of the design. FIG. 2(A) shows a structure, in the 5'UTR of the mRNA, containing a cap structure, a spacer and the Kt motif arranged from the 5' terminus, which structure is herein referred to as Sp-Kt-EGFP. FIG. 2(B) shows a structure, in the 5'UTR of the mRNA, containing a cap structure, the Kt motif and a spacer arranged from the 5' terminus, which structure is herein referred to as Kt-Sp-EGFP. Although not shown in the drawing, an mRNA containing, in the 5'UTR, a cap structure and the Kt motif arranged without providing a spacer was also designed. This structure is referred to as Kt-EGFP. The detailed sequences of the 5'UTRs of the Sp-Kt-EGFP, the Kt-Sp-EGFP and the Kt-EGFP are shown in Table 5 below. By a method described in an item (1) below, plasmids expressing these mRNAs were prepared.

In accordance with a method described in an item (2) below, a plasmid expressing L7Ae as a trigger protein was prepared, and the plasmids expressing the respective mRNAs were transfected into a cell and the translational efficiency was measured as described in items (3) to (5) below. As a result, although the expression was decreased in using the Sp-Kt-EGFP and the Kt-EGFP, the Kt-Sp-EGFP did not give such an effect. It is understood from these results that the translational repression effect of the L7Ae is reduced from 0.019 to 0.23 because of the spacer positioned between the 5' terminus and the Kt motif.

EXAMPLE 2

[Preparation of mRNAs with Position of Kt Motif from 5' Terminus Altered]

Figure 3:
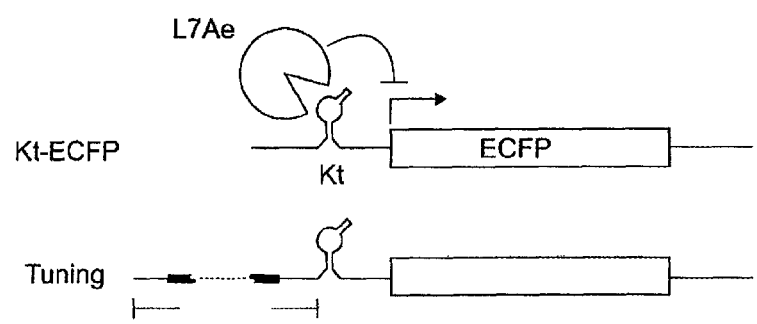
FIG. 3 is a diagram illustrating an embodiment in which a spacer is further inserted in an mRNA having a 5'UTR regulation structure comprising one Kt motif and encoding ECFP for tuning with the base length of the spacer altered.
Figure 4:
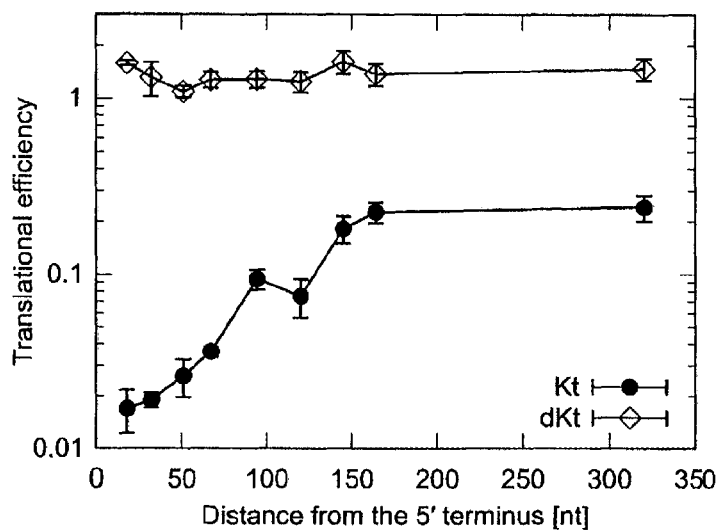
FIG. 4 is a graph illustrating relationships, obtained in an mRNA having a 5'UTR regulation structure comprising a spacer and one Kt motif and an mRNA having a 5'UTR regulation structure comprising a spacer and one dKt motif, between a distance of the corresponding motif from the 5' terminus and translational efficiency.

Next, mRNAs were designed by providing spacers so as to have the 5' terminal bases of Kt motifs positioned in the 18th, 51st, 67th, 94th, 120th, 145th and 320th bases from the 5' terminus. The number of Kt motifs for each mRNA was one. The nucleotide sequences of the 5'UTRs of the respective mRNAs are shown in Table 5 below as constructs 18nt-Kt, 51nt-Kt, 67nt-Kt, 94nt-Kt, 120nt-Kt, 145nt-Kt and 320nt-Kt. Plasmids expressing these mRNAs were prepared, so as to examine the translational efficiencies. FIG. 3 illustrates the outline of the mRNA design. As a result, in the presence of the L7Ae protein working as the trigger protein specifically binding to the Kt motif, the translational efficiency was found to be higher as the number of bases of the spacer was greater, namely, as the distance of the Kt motif from the 5' terminus was greater. Conversely, it was found that as the Kt motif is closer to the 5' terminus, the translational repression is stronger. FIG. 4 illustrates a graph of the translational efficiency against the distance of the Kt motif from the 5' terminus.

As controls, mRNAs were prepared by replacing underlined Gs and As in the nucleotide sequences of the 5'UTRs of the respective mRNAs of Table 5 by C, as constructs 18nt-dKt, 51nt-dKt, 67nt-dKt, 94nt-dKt, 120nt-dKt, 145nt-dKt and 320nt-dKt. It is known that the L7Ae protein cannot bind to mRNAs in which the underlined Gs and As are replaced by C. A dKt motif is a construct obtained by inactivating the Kt motif. The translational efficiency of these constructs was also examined in the presence of the L7Ae protein by a similar method. The results are illustrated in FIG. 4 as a similar graph of the translational efficiency. In each mRNA having the dKt motif inserted by replacing the two bases of the Kt motif by C, the translational repression was not caused regardless of the distance of the dKt motif from the 5' terminus.

TABLE 5

| construct | Sequences of the 5' UTR | Translational efficiency | SEQ ID NO |
|---|---|---|---|
| Kt-EGFP (32nt-Kt) | UCAGAUCCGCUAGCGCUACCGGACUCAGA UCUGGGGCGUGAUCCGAAAGGUGACCCG GAUCCACCGGUCGCCACCAUG | 0.019 ± 0.0019 | 19 |
| Sp-Kt-EGFP (164nt-Kt) | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCUGGGG CGUGAUCCGAAAGGUGACCCGGAUCCAC CGGUCGCCACCAUG | 0.23 ± 0.031 | 20 |
| Kt-Sp-EGFP | UCAGAUCCGCUAGCGCUACCGGACUCAGA UCUGGGGCGUGAUCCGAAAGGUGACCCG GAUCCGAUCCCGUCGUUUUACAACGUCG UGACUGGGAAAACCCUGGCGUUACCCAA CUUAAUCGCCUUGCAGCACAUCCCCCUU UCGCCAGCUGGCGUAAUAGCGAAGAGGC CCGCACCGAUCGCCCUUCCCAACAGUUGC GCAGCCUGACCGGUCGCCACCAUG | 0.029 ± 0.0042 | 21 |
| 18nt-Kt | UCAGAUCCGCUAGGAUCUGGGGCGUGAU CCGAAAGGUGACCCGGAUCCACCGGUCG CCACCAUG | 0.017 ± 0.0047 | 22 |
| 51nt-Kt | UCAGAUCCGCUAGCCGCCUGUUUUGACC GCUGGGAUCUGCCAUUGAGAUCUGGGGC GUGAUCCGAAAGGUGACCCGGAUCCACC GGUCGCCACCAUG | 0.026 ± 0.0065 | 23 |
| 67nt-Kt | UCAGAUCCGCUAGCCCGACCGCCUUACU GCCGCCUGUUUUGACCGCUGGGAUCUGC CAUUGAGAUCUGGGGCGUGAUCCGAAAG GUGACCCGGAUCCACCGGUCGCCACCAUG | 0.036 ± 0.0024 | 24 |
| 94nt-Kt | UCAGAUCCGCUAGCUCGGAUUAGGGCCG CAAGAAAACUAUCCCGACCGCCUUACUG CCGCCUGUUUUGACCGCUGGGAUCUGCC AUUGAGAUCUGGGGCGUGAUCCGAAAGG UGACCCGGAUCCACCGGUCGCCACCAUG | 0.094 ± 0.012 | 25 |
| 120nt-Kt | UCAGAUCCGCUAGCGCAGGUAGCAGAGC GGGUAAACUGGCUCGGAUUAGGGCCGCA AGAAAACUAUCCCGACCGCCUUACUGCC GCCUGUUUUGACCGCUGGGAUCUGCCAU UGAGAUCUGGGGCGUGAUCCGAAAGGUG ACCCGGAUCCACCGGUCGCCACCAUG | 0.075 ± 0.019 | 26 |
| 145nt-Kt | UCAGAUCCGCUAGCGGAUUGGCCUGAAC UGCCAGCUGGCGCAGGUAGCAGAGCGGG UAAACUGGCUCGGAUUAGGGCCGCAAGA AAACUAUCCCGACCGCCUUACUGCCGCC UGUUUUGACCGCUGGGAUCUGCCAUUGA GAUCUGGGGCGUGAUCCGAAAGGUGACC CGGAUCCACCGGUCGCCACCAUG | 0.18 ± 0.032 | 27 |
| 320nt-Kt | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCCGAUC CCGUCGUUUUACAACGUCGUGACUGGGA AAACCCUGGCGUUACCCAACUUAAUCGC CUUGCAGCACAUCCCCCUUUCGCCAGCU GGCGUAAUAGCGAAGAGGCCCGCACCGA UCGCCCUUCCCAACAGUUGCGCAGCCUG ACCGGUAGAUCUGGGGCGUGAUCCGAAA GGUGACCCGGAUCCACCGGUCGCCACCAUG | 0.24 ± 0.040 | 28 |

In Table 5, an initiation codon is shown in bold. Besides, BglII site and BamHI site corresponding to both ends of the Kt motif are shown in italics. Each underlined base is a base replaced by C for inactivating a Kt motif into a dKt motif.

It is revealed from these results that the binding between the mRNA encoding the target protein and the L7Ae working as the trigger protein is indispensable to the translational regulation for the target protein according to the present invention, and that a distance between the open reading frame and the 5' terminus of the mRNA, namely, the spacer, is not an indispensable element. It was also understood that the translational efficiency is increased substantially in proportion to the length of the spacer even when the expression level (the abundance) of the L7Ae is constant. In other words, it was understood that the translation of the target protein can be quantitatively regulated in accordance with the distance between the 5' terminus of the mRNA and the RNA motif (the Kt motif).

EXAMPLE 3

[Two-Dimensional Approach]

Figure 5A:
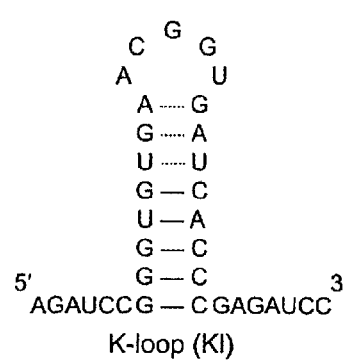
FIGS. 5(A) and 5(B) are diagrams illustrating secondary structures of a Kl motif and a Kl2 motif, that is, variants of the Kt motif

It was found, as a result of Examples 1 and 2, that the translational repression attained by the Kt motif and the L7Ae is approximately 2% to approximately 20%. If the Kt motif is away from the 5' terminus of the mRNA by 164 or more bases, further repression cannot be attained but the translational efficiency is approximately 20%. In this example, in order to expand the translational regulatable range, an mRNA into which a K-loop RNA motif was inserted instead of the Kt motif was used. FIG. 5(A) illustrates the structure of the K-loop RNA motif. The K-loop RNA motif is hereinafter referred to as the Kl motif. It is known that the Kl motif has binding affinity to the L7Ae approximately 500 times as weak as that of the Kt motif. Accordingly, the translational repression in the presence of L7Ae attained by the mRNA containing the Kl motif is weaker than the translational repression in the presence of L7Ae attained by the mRNA under the same conditions except that the Kt motif is used instead of the Kl motif.

The present inventors prepared multiple mRNAs each containing the Kl motif FIGS. 6(A), 6(B) and 6(C) illustrate the outline of the preparation. Specifically, an mRNA provided with one Kl motif (FIG. 6(A)), an mRNA provided with two Kl motifs (FIG. 6(B)) and an mRNA provided with three, four or more Kl motifs (FIG. 6(C)) were prepared. Furthermore, sixteen mRNAs were prepared by setting the distances of the Kl motif positioned closest to the 5' terminus from the 5' terminus respectively to 18 bases, 67 bases, 120 bases and 164 bases with the initiation codon, the open reading frame and the structure of the 3'UTR set to be the same in these mRNAs. Table 6 below shows the details of these mRNAs. When multiple Kl motifs were contained, a distance between the adjacent Kl motifs was set to 6 bases.

TABLE 6

| construct | Sequences of the 5' UTR | Translational efficiency | SEQ ID NO |
|---|---|---|---|
| 18nt-1xK1 | UCAGAUCCGCUAGGAUCCGGGUGUGAAC<br>GGUGAUCACCCGAGAUCCACCGGUCGCC<br>ACCAUG | 0.28 ± 0.071 | 29 |
| 18nt-2xK1 | UCAGAUCCGCUAGGAUCCGGGUGUGAAC<br>GGUGAUCACCCGAGAUCCGGGUGUGAAC<br>GGUGAUCACCCGAGAUCCACCGGUCGCC<br>ACCAUG | 0.084 ± 0.014 | 30 |
| 18nt-3xK1 | UCAGAUCCGCUAGGAUCCGGGUGUGAAC<br>GGUGAUCACCCGAGAUCCGGGUGUGAAC<br>GGUGAUCACCCGAGAUCCGGGUGUGAAC<br>GGUGAUCACCCGAGAUCCACCGGUCGCC<br>ACCAUG | 0.039 ± 0.013 | 31 |
| 18nt-4xK1 | UCAGAUCCGCUAGGAUCCGGGUGUGAAC<br>GGUGAUCACCCGAGAUCCGGGUGUGAAC<br>GGUGAUCACCCGAGAUCCGGGUGUGAAC<br>GGUGAUCACCCGAGAUCCGGGUGUGAAC<br>GGUGAUCACCCGAGAUCCACCGGUCGCC<br>ACCAUG | 0.069 ± 0.011 | 32 |
| 67nt-1xK1 | UCAGAUCCGCUAGCCCGACCGCCUUACU<br>GCCGCCUGUUUUGACCGCUGGGAUCUGC<br>CAUUGAGAUCC<u>GGGUGUGAACGGUGAUC<br>ACCCGAGAUCCACCGGUCGCCACC</u>AUG | 0.41 ± 0.060 | 33 |
| 67nt-2xK1 | UCAGAUCCGCUAGCCCGACCGCCUUACU<br>GCCGCCUGUUUUGACCGCUGGGAUCUGC<br>CAUUGAGAUCC<u>GGGUGUGAACGGUGAUC<br>ACCCGAGAUCCGGGUGUGAACGGUGAUC<br>ACCCGAGAUCCACCGGUCGCCACC</u>AUG | 0.25 ± 0.027 | 34 |
| 67nt-3xK1 | UCAGAUCCGCUAGCCCGACCGCCUUACU<br>GCCGCCUGUUUUGACCGCUGGGAUCUGC<br>CAUUGAGAUCC<u>GGGUGUGAACGGUGAUC<br>ACCCGAGAUCCGGGUGUGAACGGUGAUC<br>ACCCGAGAUCCGGGUGUGAACGGUGAUC<br>ACCCGAGAUCCACCGGUCGCCACC</u>AUG | 0.15 ± 0.015 | 35 |
| 67nt-4xK1 | UCAGAUCCGCUAGCCCGACCGCCUUACU<br>GCCGCCUGUUUUGACCGCUGGGAUCUGC<br>CAUUGAGAUCC<u>GGGUGUGAACGGUGAUC<br>ACCCGAGAUCCGGGUGUGAACGGUGAUC | 0.12 ± 0.018 | 36 |

TABLE 6-continued

| construct | Sequences of the 5' UTR | Translational efficiency | SEQ ID NO |
|---|---|---|---|
| | ACCCGAGAUCCGGGUGUGAACGGUGAUC ACCCGAGAUCCGGGUGUGAACGGUGAUC ACCCGAGAUCCACCGGUCGCCACCAUG | | |
| 120nt-1xK1 | UCAGAUCCGCUAGCGCAGGUAGCAGAGC GGGUAAACUGGCUCGGAUUAGGGCCGCA AGAAAACUAUCCCGACCGCCUUACUGCC GCCUGUUUUGACCGCUGGGAUCUGCCAU UGAGAUCCGGGUGUGAACGGUGAUCACC CGAGAUCCACCGGUCGCCACCAUG | 0.67 ± 0.059 | 37 |
| 120nt-2xK1 | UCAGAUCCGCUAGCGCAGGUAGCAGAGC GGGUAAACUGGCUCGGAUUAGGGCCGCA AGAAAACUAUCCCGACCGCCUUACUGCC GCCUGUUUUGACCGCUGGGAUCUGCCAU UGAGAUCCGGGUGUGAACGGUGAUCACC CGAGAUCCGGGUGUGAACGGUGAUCACC CGAGAUCCACCGGUCGCCACCAUG | 0.31 ± 0.031 | 38 |
| 120nt-3xK1 | UCAGAUCCGCUAGCGCAGGUAGCAGAGC GGGUAAACUGGCUCGGAUUAGGGCCGCA AGAAAACUAUCCCGACCGCCUUACUGCC GCCUGUUUUGACCGCUGGGAUCUGCCAU UGAGAUCCGGGUGUGAACGGUGAUCACC CGAGAUCCGGGUGUGAACGGUGAUCACC CGAGAUCCGGGUGUGAACGGUGAUCACC CGAGAUCCACCGGUCGCCACCAUG | 0.19 ± 0.015 | 39 |
| 120nt-4xK1 | UCAGAUCCGCUAGCGCAGGUAGCAGAGC GGGUAAACUGGCUCGGAUUAGGGCCGCA AGAAAACUAUCCCGACCGCCUUACUGCC GCCUGUUUUGACCGCUGGGAUCUGCCAU UGAGAUCCGGGUGUGAACGGUGAUCACC CGAGAUCCGGGUGUGAACGGUGAUCACC CGAGAUCCGGGUGUGAACGGUGAUCACC CGAGAUCCGGGUGUGAACGGUGAUCACC CGAGAUCCACCGGUCGCCACCAUG | 0.12 ± 0.0052 | 40 |
| 164nt-1xK1 | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCCGGGU GUGAACGGUGAUCACCCGAGAUCCACCG GUCGCCACCAUG | 0.58 ± 0.087 | 41 |
| 164nt-2xK1 | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCCGGGU GUGAACGGUGAUCACCCGAGAUCCGGGU GUGAACGGUGAUCACCCGAGAUCCACCG GUCGCCACCAUG | 0.34 ± 0.044 | 42 |
| 164nt-3xK1 | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCCGGGU GUGAACGGUGAUCACCCGAGAUCCGGGU GUGAACGGUGAUCACCCGAGAUCCGGGU GUGAACGGUGAUCACCCGAGAUCCACCG GUCGCCACCAUG | 0.21 ± 0.021 | 43 |
| 164nt-4xK1 | UCAGAUCCGCUAGCGAUACACCGCAUCC GGCGCGGAUUGGCCUGAACUGCCAGCUG GCGCAGGUAGCAGAGCGGGUAAACUGGC UCGGAUUAGGGCCGCAAGAAAACUAUCC CGACCGCCUUACUGCCGCCUGUUUUGAC CGCUGGGAUCUGCCAUUGAGAUCCGGGU GUGAACGGUGAUCACCCGAGAUCCGGGU GUGAACGGUGAUCACCCGAGAUCCGGGU | 0.17 ± 0.012 | 44 |

TABLE 6-continued

| construct | Sequences of the 5' UTR | Translational efficiency | SEQ ID NO |
|---|---|---|---|
| | GUGAACGGUGAUCACCCGAGAUCCGGGU GUGAACGGUGAUCACCCGAGAUCCACCG GUCGCCACCAUG | | |

In Table 6, the initiation codon is shown in bold, and each underlined portion corresponds to the K1 motif.

Figure 8:
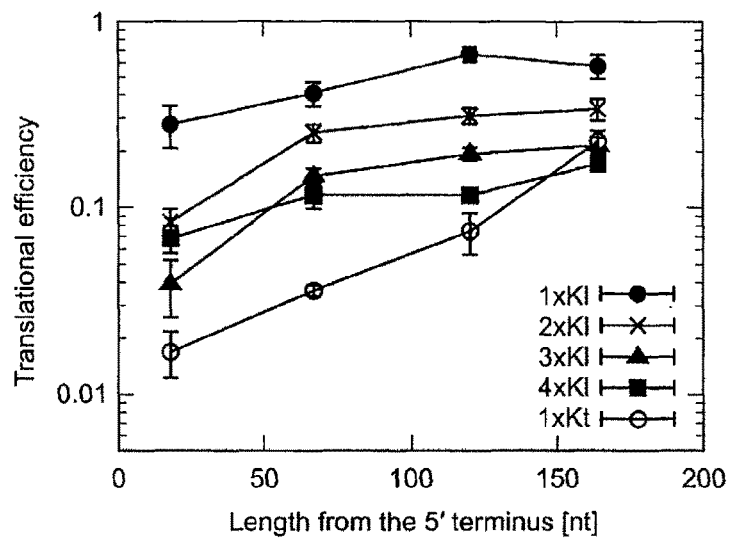
FIG. 8 is a graph illustrating relationships, obtained in an mRNA having a 5'UTR regulation structure comprising a spacer and a Kl motif and an mRNA having a 5'UTR regulation structure comprising a spacer and a Kt motif, among the number of motifs, the length of the spacer (i.e., a distance of the corresponding motif from the 5' terminus) and the translational efficiency.

The translational efficiency of these sixteen mRNAs was measured in the same manner as in Examples 1 and 2. The results are shown in FIGS. 7 and 8. It is understood, as illustrated in graphs of FIGS. 7 and 8, that the translational efficiency of the EGFP is more decreased as the number of K1 motifs is larger and as the K1 motif is positioned closer to the 5' terminus of the mRNA. In other words, it was found that the translational efficiency can be rather precisely controlled by using two parameters, the number of inserted K1 motifs and the insertion position of the K1 motif. In FIG. 8, the translational efficiency of an mRNA into which one Kt motif was similarly inserted instead of the K1 motif is also shown in the graph for comparison. In the sixteen mRNAs into which the K1 motifs were inserted, the translational regulatable range for the target protein was approximately 3% to approximately 75%.

Figure 5B:
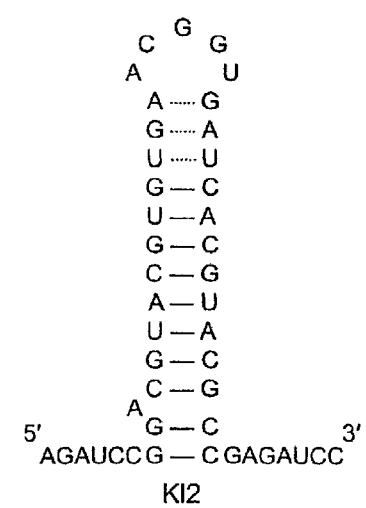

Furthermore, an mRNA into which a Kink loop 2 motif obtained by modifying the K1 motif was similarly inserted was designed, and a plasmid was constructed. The Kink loop 2 motif is hereinafter referred to as the K12 motif FIG. 5(B) illustrates the structure of the K12 motif. In this experiment, two mRNAs were designed. In one of the mRNAs, one K12 motif was inserted at the 32th base from the 5' terminus of the mRNA. The other was designed to contain two K12 motifs with a distance of the K1 motif positioned closer to the 5' terminus from the 5' terminus set to 32nd base from the 5' terminus. The details of the mRNAs are shown in Table 7 below. The open reading frame was set to encode the ECFP gene. A vector was prepared for each of the mRNAs, transfected into a cell in which the L7Ae or MS2CP was present, and the translational efficiency was measured by the flow cytometry. As a result of three experiments, the average translational efficiency of the mRNAs into which one K12 motif was inserted was 0.84, whereas the average translational efficiency of the mRNAs into which two K12 motifs were inserted was 0.093.

In Table 7, an initiation codon is shown in bold, and each underlined portion corresponds to the K12 motif.

Figure 10:
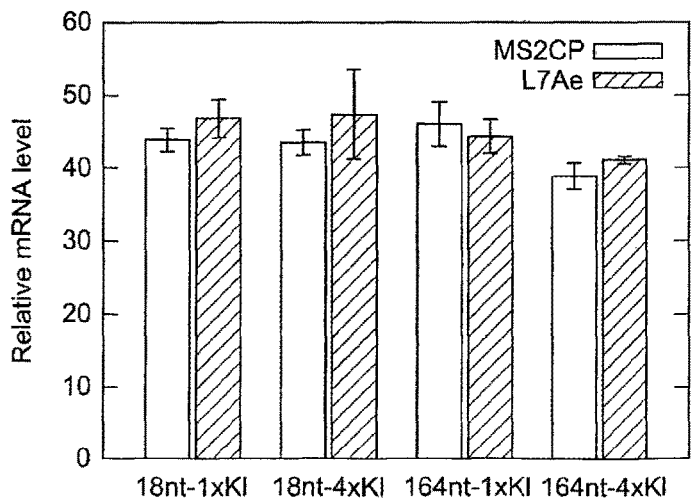
FIG. 10 is a diagram of relative mRNA levels, attained after transcription, of four mRNAs having different 5'UTR regulation structures.

In order to confirm whether the expression of a reporter gene was regulated after transcription, the amount of a designed mRNA temporarily expressed in a cell was measured by real time quantitative PCR. In this experiment, four mRNAs in which one or four K1 motifs were inserted and a distance from the 5' terminus of the K1 motif positioned closest to the 5' terminus was 18 bases or 164 bases were used for the measurement. The results are shown in FIG. 10. It was confirmed, based on a graph of FIG. 10, that the relative transcription level of the mRNA is affected by neither the structure of the 5'UTR nor the binding of a trigger protein.

EXAMPLE 4

[Simultaneous Control of Two Different mRNAs in Single Cell]

Figure 9:
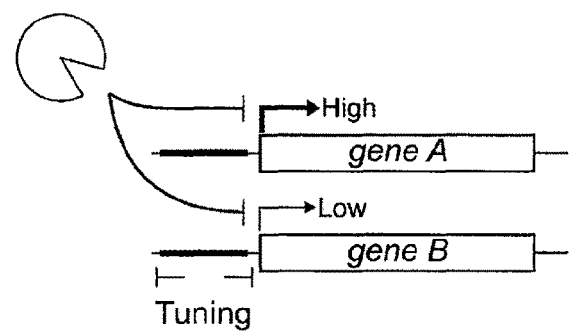
FIG. 9 is a conceptual diagram illustrating a system for simultaneously and independently regulating, in the presence of a single trigger protein, translation of two mRNAs different from each other in the structure of a 5'UTR regulation structure and a target protein to encode.

Next, it was examined whether or not a single trigger protein of an effector molecule can simultaneously and independently regulate expression of multiple genes respectively having differently controlled cis-regulatory factors. FIG. 9 is a conceptual diagram of this experiment. A plasmid set composed of a first reporter plasmid and a second reporter plasmid respectively encoding mRNAs that respectively have RNA motifs specifically binding to the same trigger protein but are different in the structure of the 5'UTR regulation structure was designed. These plasmids were transfected into a cell in which the trigger protein specifically binding to the RNA motif was present and into a cell in which the trigger protein was absent. The first reporter plasmid was an mRNA encoding an EGFP and having one Kt motif or dKt motif in the 5' position (see the structure of FIG. 2(A)). The second reporter plasmid was an mRNA encoding an ECFP (enhanced cyan fluorescent protein) and having, in the 5'UTR, a K1 motif two-dimensionally arranged as one used in Example 3. Respective sets of the

TABLE 7

| construct | Sequences of the 5' UTR | Translational efficiency | SEQ ID NO |
|---|---|---|---|
| K12 | UCAGAUCCGCUAGCGCUACCGGACUCAG AUCCGGACGUACGUGUGAACGGUGAUCA CGUACGCCGAGAUCCACCGGUCGCCACC AUG | 0.84 ± 0.0019 | 45 |
| 2xK12 | UCAGAUCCGCUAGCGCUACCGGACUCAG AUCCGGACGUACGUGUGAACGGUGAUCA CGUACGCCGAGAUCCGGACGUACGUGUG AACGGUGAUCACGUACGCCGAGAUCCAC CGGUCGCCACCAUG | 0.093 ± 0.0064 | 46 | first reporter plasmid and the second reporter plasmid were constructed so as to express mRNAs having expression efficiency regulated respectively at three stages. Constructs with low expression efficiency were Kt-EGFP and 18nt-3xKl-ECFP, constructs with high expression efficiency were dKt-EGFP and 120nt-1xKl-ECFP, and constructs with intermediate expression efficiency were Sp-Kt-EGFP and 67nt-3xKl-ECFP. They are shown in Table 8 below. These nine sets are respectively designated by using numbers shown in Table 8.

TABLE 8

|  | Kt-EGFP | Sp-Kt-EGFP | dKt-EGFP |
|---|---|---|---|
| 120nt-1xKl-ECFP | (1) | (4) | (7) |
| 67nt-3xKl-ECFP | (2) | (5) | (8) |
| 18nt-3xKl-ECFP | (3) | (6) | (9) |

Figure 11:
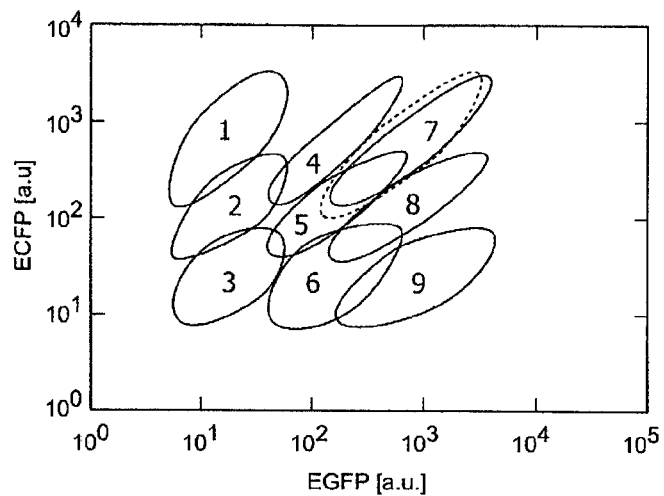
FIG. 11 is a diagram illustrating fluorescence profiles of EGFP and ECFP obtained by simultaneously expressing nine sets of mRNAs each set of which is composed of two mRNAs different from each other in the 5'UTR regulation structure and the target protein gene.

In the absence of the L7Ae protein functioning as the trigger protein for both the Kt motif and the Kl motif, the EGFP and the ECFP were uniformly expressed in all the cells transfected with the nine sets and the expression was not affected by the different structures of the 5'UTRs. On the other hand, in the presence of the L7Ae protein, the expression efficiency of the EGFP and the ECFP differs depending upon the structures of the 5'UTRs of the respective mRNAs, and nine different fluorescence profiles were obtained. The results are shown in FIG. 11. Respective numbers shown in FIG. 11 correspond to the sets numbered in Table 8 above. The output of each mRNA, namely, the amount of protein produced by the translation of each mRNA, is different from the outputs of the other mRNAs, and this means that the L7Ae protein can simultaneously and independently regulate the translation of the two mRNAs different in the 5'UTR regulation structure and in the target protein gene.

EXAMPLE 5

[Approach Using Another RNP Motif]

Next, an experiment was carried out for confirming whether or not this translational repression can be similarly exhibited in an mRNA provided with another RNP motif in the 5'UTR regulation structure. This example shows that similar effects can be attained also in a combination of the MS2 coat protein and an RNA motif specifically binding thereto and a combination of the *Bacillus* ribosomal protein S15 and an RNA motif specifically binding thereto.

(a) MS2 Coat Protein

Figure 12A:
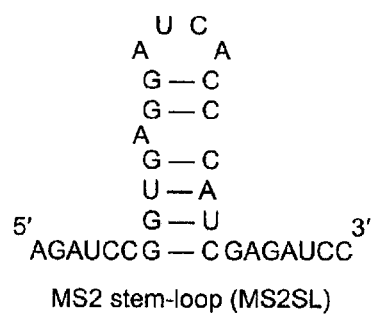
FIGS. 12(A) and 12(B) are diagrams illustrating secondary structures of an MS2SL motif and an Fr15 motif

FIG. 12(A) illustrates a secondary structure of an MS2 stem-loop motif, that is, an RNA motif to which the MS2 coat protein specifically binds. The MS2 stem-loop motif is hereinafter referred to as the MS2SL motif. Four mRNAs each provided with the 5'UTR to which the MS2SL motif was inserted were prepared. The number of the inserted MS2SL motifs was altered between one and two, and a distance of the MS2SL motif positioned closest to the 5' terminus from the 5' terminus was altered between 18 bases and 67 bases. The open reading frame and the structure of the 3'UTR were the same in all the four mRNAs. The details are shown in Table 9 below.

TABLE 9

| construct | Sequences of the 5' UTR | Translational efficiency | SEQ ID NO |
|---|---|---|---|
| 18nt-1xMS2 SL | UCAGAUCCGCUAGGAUCCGGUGAGGAUC ACCCAUCGAGAUCCACCGGUCGCCACCA UG | 0.48 ± 0.16 | 47 |
| 18nt-2xMS2 SL | UCAGAUCCGCUAGGAUCCGGUGAGGAUC ACCCAUCGAGAUCCGGUGAGGAUCACCC AUCGAGAUCCACCGGUCGCCACCAUG | 0.18 ± 0.042 | 48 |
| 67nt-1xMS2 SL | UCAGAUCCGCUAGCCCGACCGCCUUACU GCCGCCUGUUUUGACCGCUGGGAUCUGC CAUUGAGAUCCGGUGAGGAUCACCCAUC GAGAUCCACCGGUCGCCACCAUG | 1.0 ± 0.35 | 49 |
| 67nt-2xMS2 SL | UCAGAUCCGCUAGCCCGACCGCCUUACU GCCGCCUGUUUUGACCGCUGGGAUCUGC CAUUGAGAUCCGGUGAGGAUCACCCAUC GAGAUCCGGUGAGGAUCACCCAUCGAGA UCCACCGGUCGCCACCAUG | 0.67 ± 0.22 | 50 |

In Table 9, an initiation codon is shown in bold, and each underlined portion corresponds to the MS2SL motif.

Figure 13:
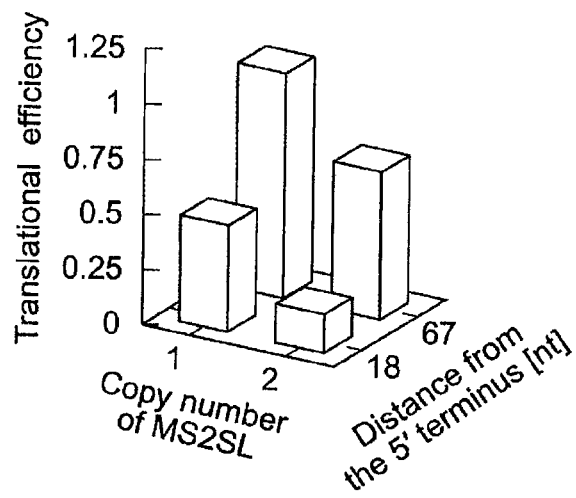
FIG. 13 is a graph illustrating relationships, obtained in an mRNA having a 5'UTR regulation structure comprising a spacer and an MS2SL motif, among the number of MS2SL motifs, the length of the spacer (i.e., a distance of the MS2SL motif from the 5' terminus) and the translational efficiency.

These four mRNAs were introduced into HeLa cells, so as to examine the translational efficiencies. FIG. 13 illustrates the result obtained by expressing the mRNAs containing the MS2SL motifs in the presence of the MS2 coat protein. It is understood, also in this case, in the same manner as in using the combination of the L7Ae protein and the Kt motif or the Kl motif, that the translational efficiency can be more decreased as the number of motifs is larger and as the insertion position of the motif is closer to the 5' terminus of the mRNA.

(b) *Bacillus* Ribosomal Protein S15

Figure 12B:
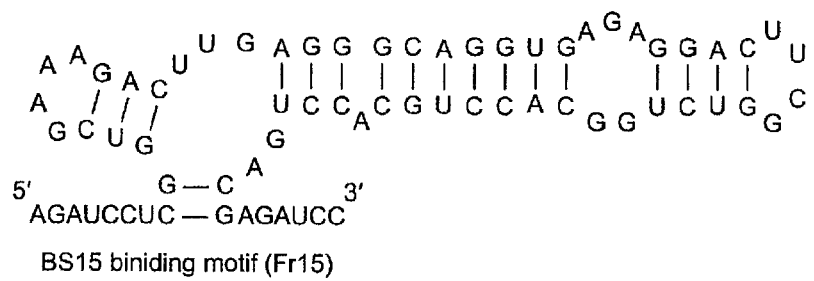

FIG. 12(B) illustrates a secondary structure of an Fr15 motif, that is, an RNA motif to which the *Bacillus* ribosomal protein S15 binds. Four mRNAs, each provided with the 5'UTR to which the Fr15 motif was inserted, were prepared. The number of the inserted Fr15 motifs was altered between one and two, and a distance of the Fr15 motif positioned closest to the 5' terminus from the 5' terminus was altered between 18 bases and 67 bases. The open reading frame and the structure of the 3'UTR were the same in all the four mRNAs. The details are shown in Table 10 below.

TABLE 10

| construct | Sequences of the 5' UTR | Translational efficiency | SEQ ID NO |
|---|---|---|---|
| 18nt-1xFr15 | UCAGAUCCGCUAGGAUCC<u>UCGGUCGAAA GACUUGAGGGCAGGAGAGGACUUCGGUC</u> UGGCCUGCACCUGACGAGAUCCACCGGU CGCCACCAUG | 0.31 ± 0.032 | 51 |
| 18nt-2xFr15 | UCAGAUCCGCUAGGAUCC<u>UCGGUCGAAA GACUUGAGGGCAGGAGAGGACUUCGGUC</u> UGGCCUGCACCUGACGAGAU<u>CCUCGGUC GAAAGACUUGAGGGCAGGAGAGGACUUC</u> GGUCUGGCCUGCACCUGACGAGAUCCAC CGGUCGCCACCAUG | 0.16 ± 0.0082 | 52 |
| 67nt-1xFr15 | UCAGAUCCGCUAGCCCGACCGCCUUACU GCCGCCUGUUUUGACCGCUGGGAUCUGC CAUUGAGAU<u>CCUCGGUCGAAAGACUUGA GGGCAGGAGAGGACUUCGGUCUGG</u>CCUG CACCUGACGAGAUCCACCGGUCGCCACC AUG | 0.45 ± 0.10 | 53 |
| 67nt-2xFr15 | UCAGAUCCGCUAGCCCGACCGCCUUACU GCCGCCUGUUUUGACCGCUGGGAUCUGC CAUUGAGAU<u>CCUCGGUCGAAAGACUUGA GGGCAGGAGAGGACUUCGGUCUGG</u>CCUG CACCUGACGAGAU<u>CCUCGGUCGAAAGAC UUGAGGGCAGGAGAGGACUUCGGUCUGG</u> CCUGCACCUGACGAGAUCCACCGGUCGC CACCAUG | 0.22 ± 0.030 | 54 |

In Table 10, an initiation codon is shown in bold, and each underlined portion corresponds to the Fr15 motif.

Figure 14:
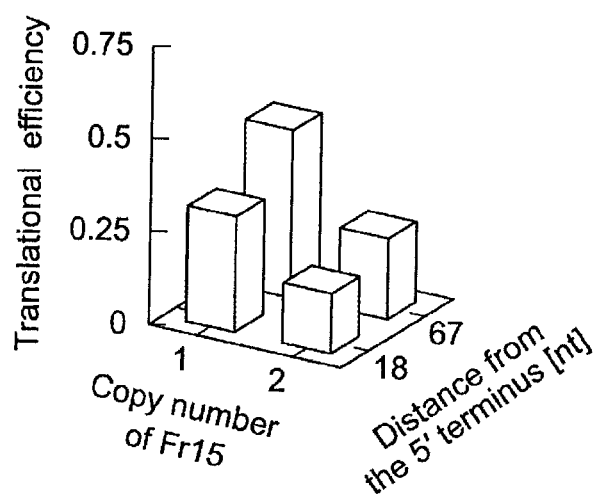
FIG. 14 is a graph illustrating relationships, obtained in an mRNA having a 5'UTR regulation structure comprising a spacer and an Fr15 motif, among the number of Fr15 motifs, the length of the spacer (i.e., a distance of the Fr15 motif from the 5' terminus) and the translational efficiency.
Figure 15:
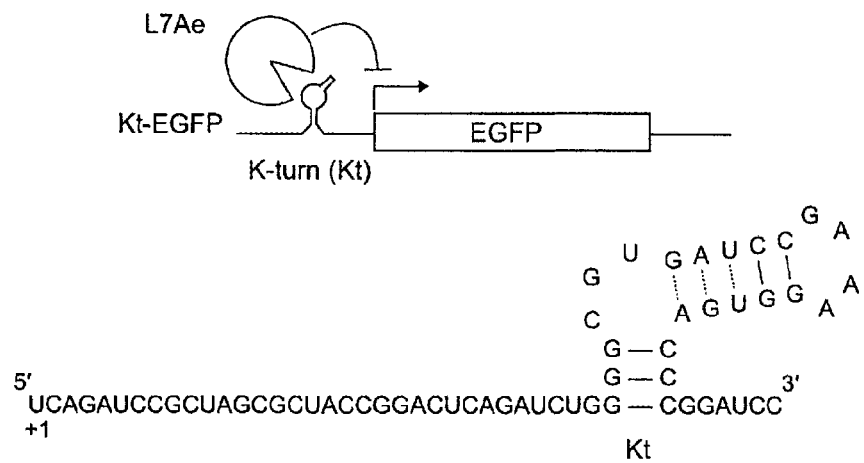
FIG. 15 is a conceptual diagram of a structure of a kink-turn RNA motif and a translation OFF switch system of the prior art using a target mRNA into which the kink-turn RNA motif is incorporated (SEQ ID NO:84).
Figure 16:
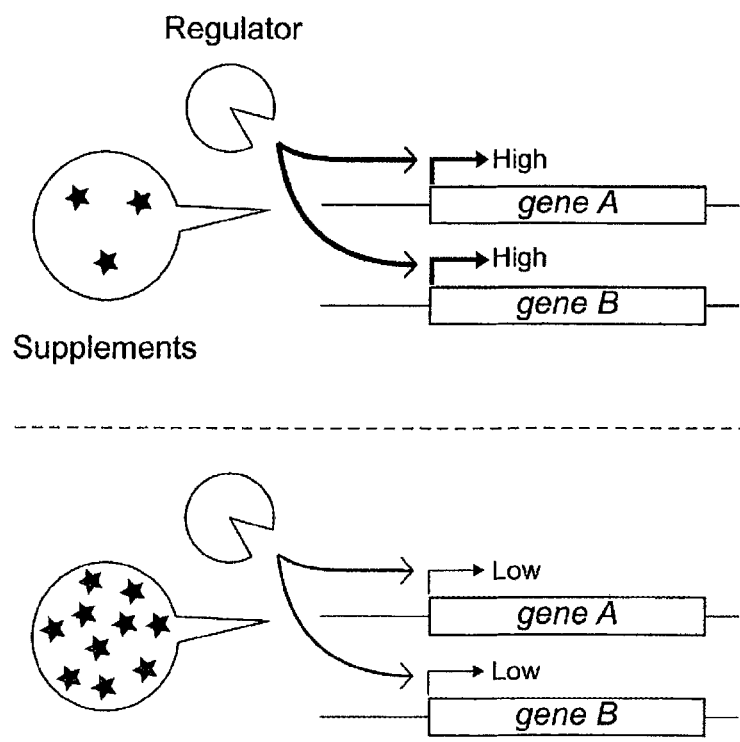
FIG. 16 is a conceptual diagram illustrating a conventional system for equally regulating transcription levels of multiple target genes in a cell by using a combination of effector molecules and transcription factor, which reveals that the activity of the transcription factor is determined depending upon the concentration of effector molecules.

In the same manner as described in the item (a), these four mRNAs were introduced into HeLa cells, so as to examine the translational efficiencies. FIG. 14 illustrates the result obtained by expressing the mRNAs containing the Fr15 motifs in the presence of the *Bacillus* ribosomal protein S15. It is understood, in the same manner as described in the item (a), that the translational efficiency can be more decreased as the number of Fr15 motifs is larger and as the insertion position of the Fr15 motif is closer to the 5' terminus of the mRNA.

It is understood from the results of Example 5 that the translational efficiency can be quantitatively regulated not only in using the Kt motif, that is, the RNA binding motif of the L7Ae protein, and its variants, the Kl motif and the Kl2 motif, but also in using a combination of another RNA-protein complex motif-derived RNA motif and a protein specifically binding thereto.

EXAMPLE 6

[Preparation of mRNA Having Inverter ON Switch Cassette]

As illustrated in FIGS. 17(A) and 17(B), a cassette composed of a bait ORF (hRluc gene in this case), β globin intron and IRES was inserted between an RNA motif of Kt-EGFP (32nt-Kt) and an initiation codon of a gene to be translated by the method described in the item (1) below (as an OFF switch). A cassette in which a stop codon (a premature termination codon (PTC)) was inserted at the 457th base and 466th base (tandem PTCs) from the initiation codon of the bait ORF was also prepared (as an ON switch cassette: SEQ ID NO: 55). When the ON switch cassette is inserted into an mRNA, the bait ORF is not translated but a gene following the IRES sequence is translated by the function of the trigger protein. Accordingly, it is conceivable that a desired protein (output) can be made to be translated in the presence of the trigger protein (input). On the other hand, it is conceivable that in the absence of the trigger protein (input), although the translation of the bait ORF proceeds, since the stop codon is positioned more than 500 bp upstream of the intron, the RNA decay is caused by the nonsense mutation-dependent mRNA decay mechanism (NMD), and hence the desired protein (output) cannot be translated because of the decay of the mRNA. Accordingly, a plasmid expressing an mRNA containing the ON switch and the Kt motif or the dKt motif and a plasmid expressing an mRNA encoding L7Ae or MS2 were simultaneously introduced into a cell in a ratio of 1:0.2. Thus, merely when the Kt motif and the L7Ae were simultaneously expressed, the EGFP was expressed (FIG. 18(A)). Correspondingly to this result, the amount of mRNA measured 24 hours after introducing the plasmid by the PCR was larger when the Kt motif and the L7Ae were simultaneously expressed (FIG. 18(B)). Flow cytometry analysis revealed that cells transfected with the cognate pair of plasmids (L7Ae/ON-Kt) showed 5- to 7-fold higher levels of EGFP fluorescence in average than those with non-cognate pairs (FIG. 18(E)). These results indicate that the insertion of the ON switch cassette (cis-acting module) into the mRNA effectively inverted the OFF switch to the ON switch.

The amount of switch mRNA present 24 hours after transfection was determined via quantitative RT PCR analysis (FIG. 18(F)). As expected, the amount of ON switch mRNA in cells transfected with the cognate pairs (L7Ae/ON-Kt) was 1.7-fold higher than in cells with non-cognate pairs, showing that the inserted module increased the steady state levels of the switch mRNA in the cells.

To further investigate the molecular mechanism of the designed module, a defective module was constructed by removing the tandem PTCs, resulting in 43 nucleotide (nt) in length between the stop codon of the bait ORF and the splice site of the intron (referred to as ONn; FIG. 20(A)). ONn was inserted to the parental OFF switch and it was found that removal of PTCs increased EGFP production even in the absence of L7Ae, and therefore disrupted the ability of the inverter module (FIG. 20(A)). This suggests that basal repression of the ON switch cassette depends on PTCs.

Next, NMD regulatory protein factors (SMG1, UPF1 and UPF2) were knocked down by using short interference RNAs (siRNAs) (FIG. 20(B)). Two days after the transfection of siRNAs, the same sets of plasmids were transfected and the behavior of the inverted switches was assessed. Knockdown of these factors increased EGFP expression and diminished further up-regulation of EGFP expression in the absence and presence of L7Ae, respectively (FIG. 20(C)), indicating that inversion of the switch depends on these factors.

In addition, some construct of ON switch cassettes were produced, in which distance between PTCs and the spliced site of the module was shortened (FIG. 20(C)). Shortening the distance to 320 nt was sufficient for the module to invert the switch. However distances shorter than this, such as 160nt proved insufficient in keeping with previous evidence that the shorter distances were less effective for triggering NMD. Taken together, these results indicate that the function of this inverter module depends on the mechanism of NMD.

Subsequently, in order to confirm whether or not a similar effect can be attained by using another trigger protein, expression of the EGFP was checked by combining the Kt or Fri 5 motif and the OFF switch or the Kt or Fri 5 motif and the ON switch with the various ratio of L7Ae or the S15 (input plasmid) to ON or OFF switch (output plasmid) (FIG. 19(A)). The observed correlation between the behavior of the S15 system in the parental OFF and inverted ON switches was similar to that of the L7Ae system (FIG. 19(A); ON-Fr15 & OFF-Fr15). In addition, western blot analyses were performed to determine the input protein levels under the experimental conditions (FIGS. 19(C) and 19(D)). It was confirmed that expression level of L7Ae or S15 increases depending on the amounts of the input plasmid (0.2-5 fold to the output plasmid) and is not saturated under our experimental conditions.

Figure 22:
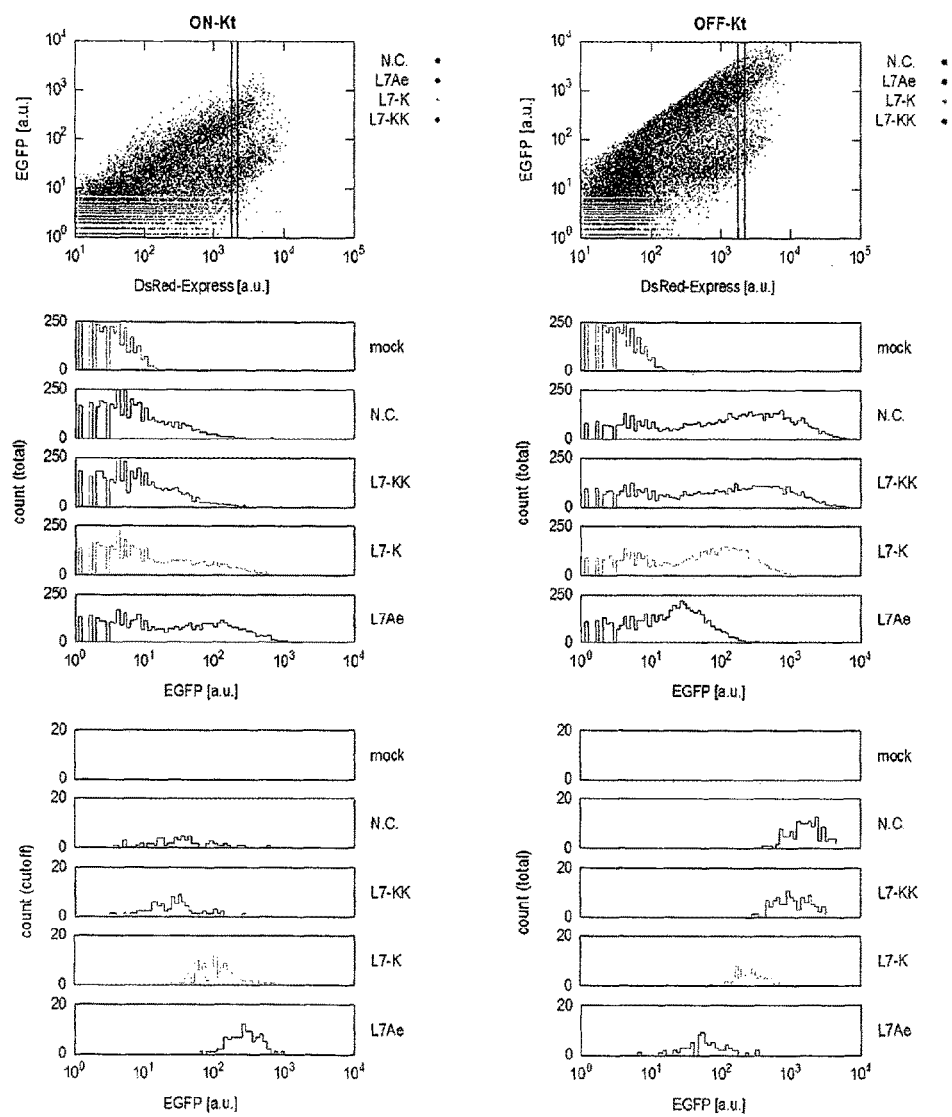
FIG. 22 is a set of graphs of flow cytometry analysis for the HeLa cells introduced with inverted switch (ON switch, ON-Kt (shown in left) or its parental OFF switch, OFF-Kt (shown in right)) and trigger protein (L7Ae or its variants (L7-K or L7-KK) or negative control (N. C.)).

Furthermore, similar experiments were carried out by using two variants of the Kt motif, that is, L7Ae (Kd value (dissociation constant) of 1.6 nM), K37A variant (L7K: Kd value of 15 nM) and K78A double variant (L7KK: Kd value of 680 nM). Thus, it was observed that as the dissociation constant was greater, the expression of the EGFP was decreased in using the ON switch and the expression was increased in using the OFF switch (FIG. 19(B) and FIG. 22). These data indicate that the switch-inverting module can universally derive ON switches from parental OFF switches. The ON and OFF switches show similar efficiencies in responding to the same input in relation to the amount of the input molecule and the affinity of the interaction between the input and the sensory RNA motif.

Figure 23A:
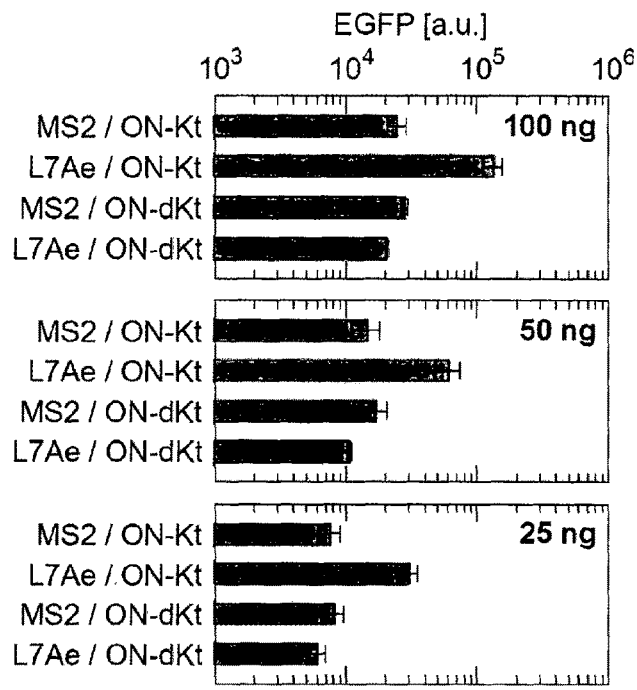
FIG. 23(A) is a set of graphs illustrating the mean intensity of EGFP fluorescence in the cells introduced with each amount of the plasmids (100 ng, 50 ng or 25 ng) expressing inverted switches (ON-Kt or ON-dKt)
Figure 23B:
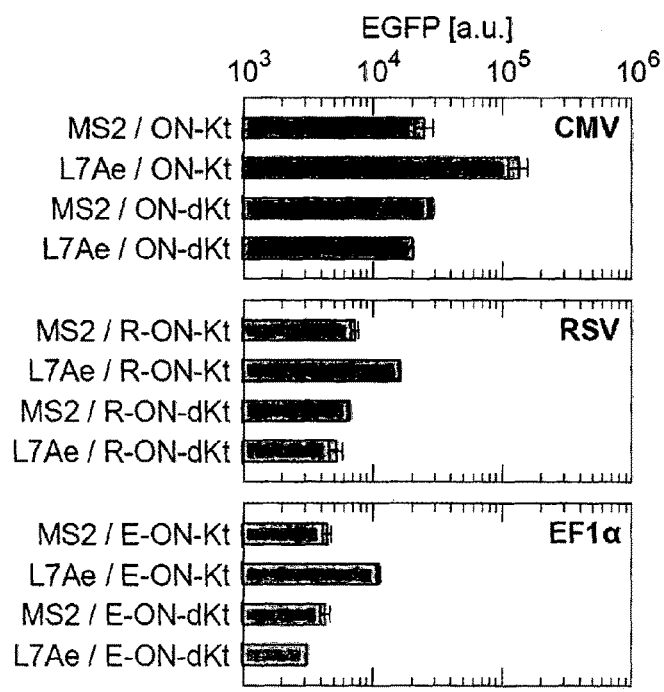
FIG. 23(B) is a set of graphs illustrating the mean intensity of EGFP fluorescence in the cells introduced inverted switches with the plasmids having different promoters (CMV (ON-Kt or ON-dKt), RSV promoter (R-ON-Kt or R-ON-dKt) or EF1α promoter (E-ON-Kt or E-ON-dKt)).

Ideally, the response of the inverted switch to the input signal should be exactly the opposite of the response of the parental switch. The dynamic range between the basal (repressed) and fully released state of the inverted ON-Fr15 switch was similar to that between the basal (released) and fully repressed state of the parental OFF-Fr15 switch (FIG. 19(A)). In contrast, the absolute output values corresponding to the repressed and released states of the two switches were different under the same conditions. If the absolute values after the conversion need to be adjusted for some applications, the mRNA levels in a cell can be optimized by altering the strength of the promoter or the efficiency of plasmid uptake; this procedure will likely compensate for the difference by vertically shifting the curves shown in FIG. 19(A). In fact, dilution of the output plasmids altered the absolute values of EGFP expression but maintained similar dynamic range before and after the inversion, suggesting that NMD component is not saturated under the Example conditions (FIG. 23(A)). It also revealed that this module is effective under the control of alternative promoters such as RSV promoter or EF1α promoter in addition to CMV promoter (FIG. 23(B)). These promoters altered the level of EGFP expression while maintaining a similar fold change before and after the inversion as in the case of plasmid dilution, indicating that output protein level from an inverted switch can be tuned by employing different promoters and/or the different concentration of the plasmids.

The minimum and maximum limits of the output expression determine the usable range of the inverted switch. In the case of the L7Ae-responsive switches described above, the corresponding usable range was narrowed after the conversion of OFF-Kt into ON-Kt (FIG. 19(A)). The response of ON-Kt reached its maximal limit at an input protein level that only suppressed OFF-Kt to half of its maximal level (corresponding to more than a 10-fold difference). The IRES-driven synthesis of the output protein is blocked after the IRES is degraded as a consequence of NMD. Therefore, very efficiently coupling NMD to IRES inactivation could reduce the minimum output level of the system. Enhancing the activity of the IRES could also improve the performance of the module by increasing the output level because IRES-driven protein synthesis is generally less effective than cap-dependent translation.

Figure 24A:
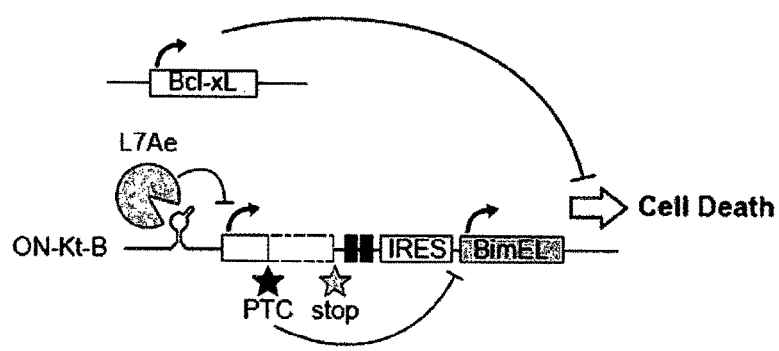
FIG. 24(A) is a conceptual diagram of plasmid expressing anti-apoptotic gene, Bcl-xL controlled by OFF switch and plasmid expressing apoptotic gene, Bim-EL instead of EGFP controlled by ON switch (ON-Kt-B)
Figure 24B:
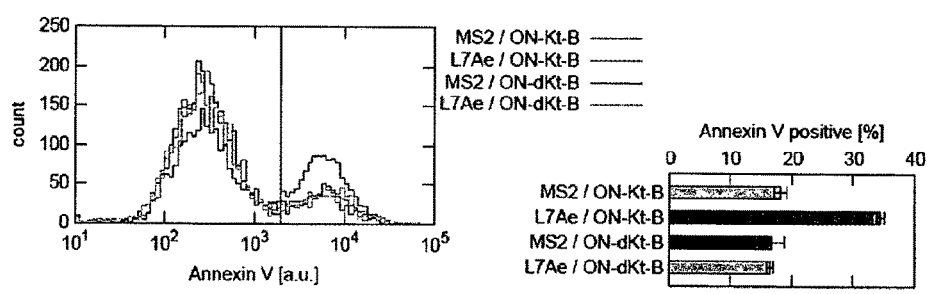
FIG. 24(B) is a graph of flow cytometry analysis for induction of Annexin V positive cells after inducing the each ON switch (ON-Kt-B or ON-dKt-B) and trigger protein (MS2 or L7Ae).

It was investigated whether our system could control a cellular phenotype via apoptosis pathways (FIG. 24(A)). It was already shown that the OFF switch could repress translation of anti-apoptotic Bcl-xL to induce apoptosis (Saito, H., et al. Nat Commun 2, 160 (2011)). Likewise, an apoptosis-controllable switch was designed, in which the output EGFP protein was replaced with pro-apoptotic Bim-EL to express Bim-EL in the input-protein, L7Ae, dependent manner (FIG. 24(A)). After the transfection of the corresponding plasmids, the number of Annexin V-positive apoptotic cells was evaluated by using a flow cytometer. As expected, Annexin V-positive cells were increased specifically when the cognate pair of the plasmids was injected (L7Ae and ON-Kt-B, FIG. 24(B)).

Figure 25A:
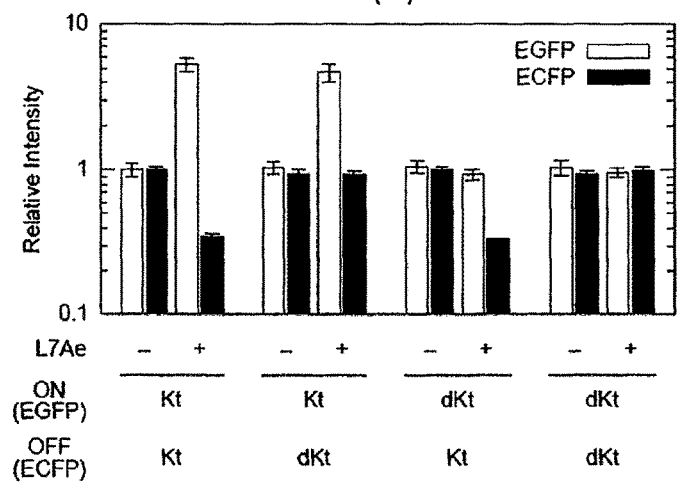
FIG. 25(A) is a graph illustrating the mean intensity of EGFP or ECFP expressed by introducing ON or OFF switches together with or without L7Ae.
Figure 25B:
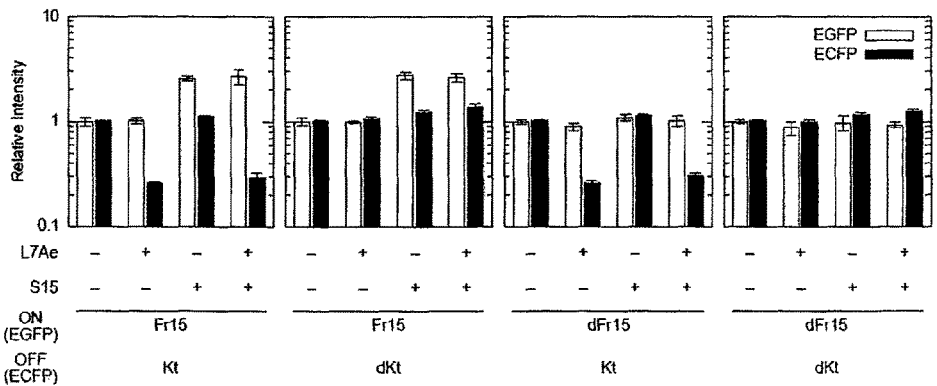
FIG. 25(B) is a set of graphs illustrating the mean intensity of EGFP or ECFP expressed by introducing ON (Fr15 and/or Kt) and OFF (dFr15 and/or dKt) switches together with or without L7Ae and/or S15.
Figures 25C, 25D:
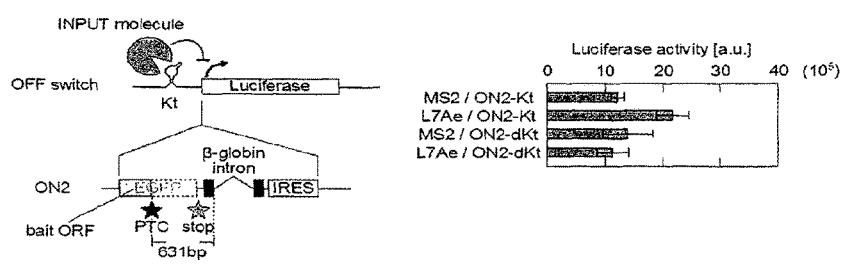
FIG. 25(C) is a conceptual diagram of the module (ON2) comprising of EGFP with PTC as a bait-ORF instead of *Renilla* luciferase.
FIG. 25(D) is a graph of luciferases activity of cells introduced with ON or OFF switch (ON2-Kt or ON2-dKt, respectively) and trigger protein (MS2 or L7Ae).

Simultaneous regulation of two independent mRNAs by the OFF switch and the ON switch was performed (FIG. 25(A)). The behavior of the inverted switches (ON-Kt or ON-dKt) and their modified parental switches (OFF-Kt or OFF-dKt) was analyzed at the same time (FIG. 25(A)). As expected, both ON and OFF switches containing Kt were specifically up- and down-regulated EGFP and ECFP as an output, respectively, in the presence of L7Ae. Notably, each OFF or ON switch incorporated into the same cell did not affect the function of its counterpart. Furthermore, an alternative ON switch utilizing another input protein, S15, was employed and it was confirmed that the OFF (OFF-Kt or OFF-dKt) and ON (ON-Fr15 or ON-dFr15) switches specifically respond to the corresponding inputs, L7Ae and S15, respectively (FIG. 25(B)).

Discussion

Signal inversion is one of the most fundamental processes in a circuit. Similar to electrical engineering, complicated biological circuits utilize many signal inversions (Stapleton, J. A. et al. ACS Synth. Biol. 1, 83-88 (2011), Xie, Z., Wroblewska, L., Prochazka, L., Weiss, R. & Benenson, Y. Science 333, 1307-1311 (2011), and Wang, B., Kitney, Joly, N. & Buck, M. Nat Commun 2, 508 (2011)). In many instances, synthetic biologists have employed trans-acting effector and sensor pairs as inverter modules. This approach requires at least one unique regulatory pair for every inversion, and performing the inversion in a cell requires a highly independent pair to avoid crosstalk between signaling circuits, which would likely represent a major problem. To avoid this potential pitfall, recent efforts have been made to generate numerous orthogonal regulatory pairs (Mutalik, V. K., Qi, L., Guimaraes, J. C., Lucks, J. B. & Arkin, A. P. Nat. Chem. Biol. 8, 447-454 (2012)). Unfortunately, while many orthogonal pairs could potentially be developed to generate new sets of trans-acting effectors and sensors, the number of such sets is finite. In contrast, the ON switches produced by the cis-acting module allow the input molecules to directly determine the output protein levels in the absence of additional factors. Moreover, the cis-acting module is advantageous when compared with trans-acting modules because it will likely enable the inversion of multiple signals with similar efficiency. The dynamic range of each inverted switch will differ and will be determined by the nature of the corresponding module in the case of trans-acting modules.

This invention succeeded in replacing the original β-globin intron (476 nt) with the shorter chimeric intron (133 nt) without sacrificing the efficiency of the inverter module (FIG. 21(B)). Moreover, the module with a shortened distance between PTC and the splice site of the intron (320nt) maintained the efficiency (FIG. 21(A)). These results indicate that more compact modules could be designed and constructed by using these elements. Furthermore, a module containing another bait ORF (the part of EGFP gene) functioned as an inverter (FIGS. 25(A) and 25(B)). Thus, a bait ORF is likely to be replaced with desired protein-coding sequences.

This module could be employed to develop new ON switches from available translational OFF switches in which the 5'-UTRs of the mRNAs respond to a variety of input molecules, including small molecules, RNA, and proteins, in eukaryotic cells (Saito, H. et al. Nat. Chem. Biol. 6, 71-78 (2010), Saito, H., Fujita, Y., Kashida, S., Hayashi, K. & Inoue, T. Nat Commun 2, 160 (2011), Werstuck, G. & Green, M. R. Science 282, 296-298 (1998), Hanson, S., Berthelot, K., Fink, B., McCarthy, J. E. & Suess, B. Mol. Microbiol. 49, 1627-1637 (2003), and Paraskeva, E., Atzberger, A. & Hentze, M. W. Proc. Natl. Acad. Sci. U.S.A. 95, 951-956 (1998)). In addition, it should also be possible for this module to invert ON switches (Schlatter, S. & Fussenegger, M. Biotechnol. Bioeng. 81, 1-12 (2003)) to OFF switches, because the IRES-driven production of an output protein from the inverted switches is inversely related to the activity of the cap-dependent translation of the bait ORF that corresponds to the output of the parental switches.

Finally, the method that we have shown in the present study enables the detection of proteins in the cytoplasm while another synthetic RNA device has been reported that can detect nuclear protein expression to control genetic circuits by employing alternative splicing (Culler, S. J., Hoff, K. G. & Smolke, C. D. Science 330, 1251-1255 (2010)). Thus, the two types of switches are now available that work in either the nucleus or cytoplasm.

The specific methods for preparing mRNAs and plasmid vectors expressing the trigger proteins and for introducing them into a cell, and various measurement methods commonly employed in Examples 1 to 6 will be described in the following.

(1) Construction of Reporter Plasmid

In these examples, the pKt-EGFP and pdKt-EGFP used as a reporter plasmid expressing the EGFP were prepared respectively correspondingly to pl boxC/D-EGFP and pl boxC/D mutEGFP described by Gossen M, Bujard H (1992) Proc Natl Acad Sci USA 89:5547-5551. With the region encoding the EGFP replaced by ECFP, pKt-ECFP and pdKt-ECFP were similarly prepared. The sequences of the 5'UTRs of the pKt-EGFP and the pKt-ECFP accord with that of the 32nt-Kt shown in Table 5 above.

The spacer sequences were amplified by the PCR from LacZ. Primer sets of (5'-CCCGGGATCCGATC-CCGTCGTTTTACAAC-3' (SEQ ID NO: 56)/5'-AGATC-TACCGGTCAGGCTGCGCAAC-3' (SEQ ID NO: 57) and 5'-GGATCCGCTAGCGATACACCGCATC-3' (SEQ ID NO: 58)/5'-ACTAGTAGATCTCAATGGCAGATCCCAG-3' (SEQ ID NO: 59) were used. A primer set is herein mentioned as a forward primer and a reverse primer in this order. The spacer sequences were digested and ligated between the BamHI-AgeI sites and the NheI-BglII sites of pKt-EGFP so as to prepare plasmids pKt-Sp-EGFP and pSp-Kt-EGFP, respectively. Similarly, pdKt-Sp-EGFP and pSp-dKt-EGFP were prepared from pdKt-EGFP.

The pKt-ECFP and pdKt-ECFP were digested with NheI and BamHI, blunted by a Klenow fragment (manufactured by Takara Bio Inc.) and self-ligated to prepare the shortest 5'UTR spacer (18 nt). The longest spacer sequence (320 nt) was obtained by concatenation of the two spacer fragments described above and inserted between the NheI-BglII sites of pKt-ECFP and pdKt-ECFP. The other spacers were obtained by amplifying appropriate primer sets inserted into the 5'UTRs of the reporter plasmids in a similar manner. The sequences of all the used 5'UTRs are shown in Table 5 above.

Pairs of oligonucleotides K1 were 5'-CATGGGATC-CGGGTGTGAACGGTGATCACCCGA-3' (SEQ ID NO: 60)/5'-GATCTCGGGTGATCACCGTTCACACCCG-GATCC-3' (SEQ ID NO: 61). Pairs of oligonucleotides K12 were 5'-CATGGGATCCGGACGTACGTGTGAACGGT-GATCACGTACGCCGA-3' (SEQ ID NO: 62)/5'-GATCTCGGCGTACGTGATCACCGTTCACACG-TACGTCCGGATCC-3' (SEQ ID NO: 63). Pairs of oligonucleotides MS2SL were 5'-CATGGGATCCGGT-GAGGATCACCCATCGA-3' (SEQ ID NO: 64)/5'-GATCTCGTTGGGTGTTCCTCTCCGGATCC-3' (SEQ ID NO: 65). These nucleotide pairs were annealed and cloned into a cloning vector. The Fr15 was amplified by the PCR from DNA templates (5'-GGGATGTCAGGTGCAGGCCA-GACCGAAGTCCTCTCCTGCCCTCAAGTCTTTCGAC CATCCCTATAGTGAGTCGTATTAGC-3' (SEQ ID NO: 66)) by using primer sets (5'-GCTAATCCATGGGATC-CTCGGTCGAAAGACTTGAGGGC-3' (SEQ ID NO: 67)/5'-CCCAGATCTCGTCAGGTGCAGGCCAGAC-3' (SEQ ID NO: 68)). The Fr15 was then digested by NcoI and BglII and cloned into the cloning vector similarly. Each RNA motif was concatenated by using BamHI at the 5' terminus and BglII at the 3' terminus of the cloning vector. Then, single or multiple RNA motifs were extracted from the cloning vector by digestion with BamHI and BglII and inserted between the BglII-BamHI sites of the vectors that contain the Kt motif at the 67th, 120th and 164th nucleotides from the 5' terminus. The same fragments of RNA motifs were also inserted into the BamHI site of pKt-ECFP and placed at the 18th nucleotide from the 5' terminus by blunting and self-ligation.

An ON switch cassette was constructed from Renilla luciferase (hRluc) with nonsense mutation, β globin intron and IRES2. Briefly, it was prepared as follows: pLP1 (Invitrogen Corporation) was digested with BamH1 and BglII, and β globin intron was extracted and inserted into the BamH1 site of pIRES2-EGFP (Clontech Laboratories, Inc.). The thus obtained plasmid was digested with BamH1, blunted by a Klenow fragment and then self-ligated to remove the BamH1 site (psBIntIRES2-EGFP). A 5'UTR digested from pl boxC/D-EGFP was inserted into NheI-NcoI site of pGL4.73, and W153 and W156 of *Renilla* luciferase were transformed into a stop codon by the PCR by using a primer set (5'-GTGACCTGACATCGAGGAGGATA-3' (SEQ ID NO: 69)/5'-TCGTCTCAGGACTCGAT-CACGTCC-3' (SEQ ID NO: 70)). Subsequently, the 5'UTR and the variant *Renilla* luciferase were inserted into the psBIntIRES2-EGFP by digestion with NheI-SmaI site, so as to prepare a plasmid having an ON switch cassette. A plasmid having an OFF switch cassette was similarly prepared by using *Renilla* luciferase not converted into a stop codon.

(2) Preparation of Trigger Plasmid

A trigger plasmid expressing a protein specifically binding to a Kt motif was prepared. The protein specifically binding to the Kt motif is fused to a One-STrEP-tag (IBA) at the N-terminus and binds to a myc-tag and His-tag at the C-terminus, and has IRES-driven DSRed Express under the control of a CMV promoter.

pIRES2-DsRed-Express was digested with BamHI and NotI, and a fragment containing the IRES2-driven DsRed-Express expression cassette was cloned into the BamHI-NotI site of pcDNA5/FRT/TO (manufactured by Invitrogen). A HindIII-digested fragment from p4LambdaN22-3mEGFP-M9 was inserted into the resulting expression vector. Then four-times repeated Lambda N22 peptide was replaced by the RNA-binding proteins that were amplified by the PCR and fused to the peptide tags. The open reading frames of *Archaeoglobus fulgidus* L7Ae were amplified by using a primer set (5'-GAATCCATGGGATCCATGTACGT-GAGATTTGAGGTTC-3' (SEQ ID NO: 71)/5'-CACCA-GATCTCTTCTGAAGGCCTTTAATCTTCTC-3' (SEQ ID NO: 72)). The open reading frames of bacteriophage MS2 coat protein were amplified by using a primer set (5'-CACCATGGGATCCGCTTCTAACTTTACTCAGTTCGT-TCTC-3' (SEQ ID NO: 73)/5'-TATGAGATCTGTAGAT-GCCGGAGTTGGC-3' (SEQ ID NO: 74)). Furthermore, the open reading frames of *Bacillus stearothermophilus* S15 were amplified by using a primer set (5'-GACAC-CATGGGATCCGCATTGACGCAAGAGCG-3' (SEQ ID NO: 75)/5'-TATGAGATCTTCGACGTAATC-CAAGTTTCTCAAC-3' (SEQ ID NO: 76)). These primers were respectively derived from a plasmid pL7Ae, a plasmid MS2-EGFP and a plasmid newly synthesized based on 25: Scott L G, Williamson J R (2001) Interaction of the *Bacillus stearothermophilus* ribosomal protein S15 with its 5'-translational operator mRNA. J Mol Biol 314:413-422.

RSV promoter and EF1α promoter were amplified via PCR using the primer sets, 5'-GAGGGGATTAATG-TAGTCTTATGCAATACTCTTGTAGTCTTGC-3' (SEQ ID NO: 85)/5'-GTTGTTGCTAGCTCGAGCTTGGAG-GTGC-3' (SEQ ID NO: 86)and 5'-GAATTCATTAATG-GCTCCGGTGCCCGTCAG-3' (SEQ ID NO: 87)/5'-AAGCTTGCTAGCTCACGACACCTGAAATGGAAGA AAAAAAC-3' (SEQ ID NO: 88), from pLP2 (Invitrogen) and KW239_p5E-hEF1α(kindly provided by Dr. K. Woltjen), respectively. They were digested by AseI and NheI for insertion into AseI-NheI site of pON-Kt/dKt to generate pR-ON-Kt/dKt and pE-ON-Kt/dKt, respectively.

Shorter modules (ON32, ON16 and ON8) were generated via PCR-based deletion method using a reverse primer (5'-TGATCAGGGCGATATCCTCCTCG-3' (SEQ ID NO: 89)) with specific forward primers (5'-GTCCAGATTGTC-CGCAACTACAACG-3' (SEQ ID NO: 90), 5'-GCCAG-GAGGACGCTCCAG-3' (SEQ ID NO: 91), and 5'-TAGAGTCGGGGCGGCCGGGATC-3' (SEQ ID NO: 92), respectively). Then, AgeI-Bsp1407I fragments of the resulting plasmids were returned into pON-Kt/dKt. To replace the intron, a chimeric intron and the hRluc gene containing PTC were amplified via PCR using a primer set: 5'-CGCAAATGGGCGGTAGGCGTG-3' (SEQ ID NO: 93)/ 5'-CATGGTTGTGGCCATATTATCATCG-3' (SEQ ID NO: 94), and 5'-CGATGATAATATGGCCACAACCATG-GCAAAGCAACCTTCTGATG-3' (SEQ ID NO: 95) /5'-GCCCCGC AGAAGGTCTAGAATCAATGCATTCTCCA-CACCAG-3' (SEQ ID NO: 96), from pRL-TK (Promega) and pON-Kt, respectively. PCR products were concatenated via PCR together with the PCR product of IRES, digested by EcoRV and HindIII, and inserted into EcoRV-HindIII site of pON-Kt/dKt. Construction of pON2-Kt and pON2-dKt was similar to that of pON-Kt and pON-dKt, except for a primer set used to generate PTC: 5'-CCCACCCTCGTGACCAC-3' (SEQ ID NO: 97)/5'-TCAGGGCACGGGCAG-3' (SEQ ID NO: 98).

IRES and Bim-EL were amplified from pIRES2-EGFP and pBim (Saito, H., Fujita, Y., Kashida, S., Hayashi, K. & Inoue, T. Nat Commun 2, 160 (2011).) via PCR using a primer set: 5'-CGCAAATGGGCGGTAGGCGTG-3' (SEQ ID NO: 99)/5'-CATGGTTGTGGCCATATTATCATCG-3' (SEQ ID NO: 100)and 5'-CGATGATAATATGGCCA-CAACCATGGCAAAGCAACCTTCTGATG-3' (SEQ ID NO: 101)/5'-GCCCCGCAGAAGGTCTAGAATCAATG-CATTCTCCACACCAG-3' (SEQ ID NO: 102), respectively. These fragments were concatenated by PCR again using a primer set: 5'-CGCAAATGGGCGGTAGGCGTG-3' (SEQ ID NO: 103)/5'-AAGCTTGCGGCCGCCCCGCA-GAAGGTCTAGA-3' (SEQ ID NO: 104), digested with HindIII and NotI, and inserted into HindIII-NotI site of pON-Kt/dKt to generate pON-Kt/dKt-B, respectively.

(3) Cell Culture and Transfections

HeLa cells were cultured at 37° C. and 5% $CO_2$ in Dulbecco's modified Eagle's medium (GIBCO, Carlsbad, Calif.) containing 10% fetal bovine serum (Nichirei Biosciences, Tokyo, Japan) and 1% antibiotic-antimycotic solution (Sigma-Aldrich, St Louis, Mo.). In all, $5 \times 10^4$ cells were seeded in 24-well plates, and after 24 hours, 70 to 90% confluent cells were transiently transfected with plasmids using 1 µl of Lipofectamine 2000 (Invitrogen, Carlsbad, Calif.) following the manufacturer's instructions. In the double-transfection experiments (Examples 1 to 3 and 5), 0.1 µg of a reporter plasmid and 0.5 µg of a trigger protein plasmid were transfected into cells. In the triple-transfection experiment (Example 4), 0.1 µg each of two reporter plasmids and 0.3 µg of a trigger protein plasmid were used. Media were changed 4 hours after the transfection.

(4) Flow Cytometric Measurement

Twenty-four hours after the transfection, cells were washed with PBS and incubated in 100 µl of 0.25% Trypsin-EDTA (GIBCO) for 2 min. at 37° C. After addition of 100 µl of the medium, cells were passed through a 35 µm strainer (BD Biosciences, San Jose, Calif.) and then analyzed with a FACS Aria (BD Biosciences). A 408 nm semiconductor laser for excitation and a 450/40 nm filter were used to measure the fluorescence of ECFP. A 488 nm semiconductor laser and 530/30 nm and 695/40 nm filters were used to measure the fluorescence of EGFP and DsRed-Express, respectively.

(5) Flow Cytometric Analysis

Dead cells were gated out by using FSC (forward scatter property) and SCC (side scatter property). In this experiment, the translational efficiency was defined as the ratio of an average of the EGFP or ECFP fluorescence intensity in the presence of RNA-binding protein (such as MC2CP), which is a negative control not binding to the RNA motif, divided by that in the presence of corresponding RNA-binding protein (such as L7Ae) from cells expressing a freely chosen 1000±100 a.u. of DsRed. In the triple-transfection, the level of fluorescence was compensated on the basis of cells respectively expressing the EGFP, the ECFP or the DsRed-Express alone. Untransfected cells were gated out based on the fluorescence level of DsRed-Express (<100 a.u.). All the experiments were repeated three times, and the average and the standard deviation are presented.

(6) Isolation of Total RNA and cDNA Synthesis

Twenty-four hours after the transfection, cells were washed with chilled PBS. Total RNA was isolated using the RNAqueous-4PCR Kit (manufactured by Ambion), following the manufacturer's instructions. In all, 350 µl of cell suspension/binding solution was used, and RNA was eluted in 50 µl of Milli-Q water twice. Contaminating DNA was removed using the TURBO DNA-free Kit (manufactured by Ambion), following the manufacturer's instructions. cDNA was synthesized from 200 ng of the extracted total RNA using High-Capacity cDNA Reverse Transcription Kits (manufactured by Applied Biosystems). Resulting cDNA solutions were diluted 10-fold, and a 5 µl aliquot was subjected to quantitative PCR analysis.

(7) Quantitative PCR Analysis

The quantitative PCR analysis was carried out using LightCycler 480 SYBR Green I Master and LightCycler 480 instruments (Roche, Basel, Switzerland). The reaction solutions contained primer sets (5'-GAAGCGCGATCA-CATGGT-3' (SEQ ID NO: 77)/5'-CCATGCCGAGAGT-GATCC-3' (SEQ ID NO: 78)) or (5'-GGCTACCCGTGATATTGCTG-3' (SEQ ID NO: 79)/5'-GCGATACCGTAAAGCACGA-3' (SEQ ID NO: 80)) at a final concentration of 500 nM to measure the RNA levels of reporter ECFP or neomycin-resistant gene, respectively. A series of 10-fold dilutions of the reporter plasmid (50 fg to 5 ng) was used as a standard. The relative amount of the reporter ECFP mRNA was determined as a ratio to that of neomycin-resistance gene that was expressed from the same plasmid as the reporter. All the experiments were repeated three times, and the average and standard deviation were presented.

(8) RNAi Knock-down

A total of $2.5 \times 10^4$ cells were seeded in 24-well plates, and after 24 hours, cells were transfected with 20 pmol of siRNA using 1 micro-1 of StemFect RNA transfection kit(Stemgent, Cambridge, Mass.) according to manufacturer's instruction. The medium was changed 4 hours after transfection. After 48 hours, a set of plasmids were transfected as described above. Then, after 24 hours, the cells were subjected to flow cytometry analysis using BD Accuri. According to the previous studies 28, the sequences of siRNA used in this experiment were as follows: 5'-GUGUAUGUGCGC-CAAAGUATT-3' (SEQ ID NO: 105)/5'-UACUUUGGCG-CACAUACACTT-3' (SMG1) (SEQ ID NO: 106), 5'-GAUGCAGUUCCGCUCCAUUTT-3' (SEQ ID NO: 107)/5'-AAUGGAGCGGAACUGCAUCTT-3' (UPF1) (SEQ ID NO: 108), 5'-CAACAGCCCUUCCAGAAUCTT-3' (SEQ ID NO: 109)/5'-GAUUCUGGAAGGGCU-GUUGTT-3' (UPF2) (SEQ ID NO: 110), and 5'-UUCUC-CGAACGUGUCACGUTT-3' (SEQ ID NO: 111)/5'-ACGUGACACGUUCGGAGAATT-3' (n.c., non-silencing negative control) (SEQ ID NO: 112).

(9) Western Blotting Analysis

Transfection experiments were performed in four times larger scale in 6-well plates compared with that in 24-well plates. After 24 hours (plasmid transfection) or 48 hours (RNAi knock-down), transfected cells were washed twice with 2 mL of PBS and extracted in 0.3 mL of RIPA buffer. Concentration of total proteins was measured by BCA Protein assay (Thermo, Rockford, Ill.). Samples (10 microg) were subjected to SDS-PAGE, transferred into a PVDF membrane using iBlot (Invitrogen) following manufacture's instruction, and probed with indicated antibodies followed by HRP-conjugated secondary antibodies. SMG1 and RENT1 antibody were purchased from Bethyl laboratories (Montgomery, Tex.). UPF2 rabbit monoclonal antibody (D3B10) was purchased from Cell Signaling laboratory (Danvers, Mass.). The blots were detected with Immobilon Western Chemiluminescent HRP Substrate (Millipore, Billerica, Mass.) and ImageQuant LAS 4000 (GE Healthcare, Piscataway, N.J.).

(10) Apoptosis Assay

Alternative INPUT plasmids, which express EGFP instead of DsRed-Express, were used in this experiment. Twenty-four hours after transfection of the plasmids, the cells and medium were collected, stained with Annexin V, Pacific Blue conjugates (Invitrogen) according to the manufactures' instruction, and analyzed using a FACSAria cell sorter. Untransfected cells were gated out based on EGFP fluorescence. The average and standard deviation from two independent experiments are presented.

The invention claimed is:
1. A translational regulation method using an RNA-protein interaction motif, comprising the step of:
introducing an mRNA having: a 5' UTR regulation structure comprising:
(1) a cap structure on the 5' terminus,
(2) one or more RNA motifs positioned on the 3' side of the cap structure, of an RNA-protein interaction motif derived-nucleotide sequence or a variant thereof, and
(3) an ON switch cassette positioned on the 3' side of the one or more RNA motifs and having a sequence comprising
(a) a bait open reading frame (a bait ORF),
(b) an intron comprising a human beta globin intron or a chimeric intron, and
(c) an internal ribosome entry site (IRES); and
a nucleotide sequence encoding a target protein gene on the 3' side of the 5' UTR regulation structure, into a cell, and
starting translation of the target protein by a protein specifically binding to the one or more RNA motifs,
wherein the bait ORF is a sequence comprising a stop codon in more than 320 bases from the intron,
wherein said ON switch cassette is positioned on
(a) 3' side of the RNA motif if the 5' UTR regulation structure comprises one RNA motif structure; or
(b) 3' side of the RNA motif positioned at 3' end of the RNA motifs if the 5' UTR regulation structure comprises two or more RNA motifs;
wherein the mRNA is an artificially prepared non-natural mRNA;
wherein said human beta globin intron comprises a nucleotide sequence of Seq. ID No. 18; wherein said chimeric intron comprises a nucleotide sequence of Seq. ID No. 83.
2. The method according to claim 1, wherein the bait ORF is a sequence comprising a stop codon inserted at the 457th base from the 5' side of *Renilla* luciferase; wherein said *Renilla* luciferase comprises a nucleotide sequence of Seq. ID No. 17 or Seq. ID No. 81.
3. The method according to claim 1, wherein the intron is human β globin intron.
4. The method according to claim 1, wherein each of the RNA motifs is a binding sequence selected from the group consisting of a binding sequence of L7Ae protein, a binding sequence of MS2 phage coat protein and a binding sequence of *Bacillus stearothermophilus* ribosomal protein S15.

* * * * *